(12) United States Patent
Annapragada et al.

(10) Patent No.: US 9,801,957 B2
(45) Date of Patent: Oct. 31, 2017

(54) LIPID-BASED NANOPARTICLES

(76) Inventors: Ananth Annapragada, Manvel, TX (US); Jason L. Eriksen, Houston, TX (US); Eric A. Tanifum, Katy, TX (US); Indrani Dasgupta, Frederick, MD (US); Stephen C. Cook, Houston, TX (US)

( * ) Notice: Subject to any disclaimer, the term of this patent is extended or adjusted under 35 U.S.C. 154(b) by 1293 days.

(21) Appl. No.: 13/441,816

(22) Filed: Apr. 6, 2012

(65) Prior Publication Data
US 2012/0258044 A1 Oct. 11, 2012

Related U.S. Application Data

(60) Provisional application No. 61/472,605, filed on Apr. 6, 2011.

(51) Int. Cl.
*A61K 49/18* (2006.01)
*A61K 47/48* (2006.01)
*A61K 49/04* (2006.01)

(52) U.S. Cl.
CPC .... *A61K 49/1812* (2013.01); *A61K 47/48815* (2013.01); *A61K 49/0466* (2013.01)

(58) Field of Classification Search
None
See application file for complete search history.

(56) References Cited

U.S. PATENT DOCUMENTS

| | | | |
|---|---|---|---|
| 5,204,085 A | 4/1993 | Vanderipe | |
| 5,676,925 A | 10/1997 | Klaveness et al. | |
| 5,676,928 A | 10/1997 | Klaveness et al. | |
| 6,171,614 B1 | 1/2001 | Chaikof et al. | |
| 6,821,504 B2 * | 11/2004 | Wisniewski | A61K 49/085 424/1.11 |
| 7,138,136 B2 | 11/2006 | Annapragada et al. | |
| 7,208,174 B2 | 4/2007 | Huwyler et al. | |
| 7,713,517 B2 | 5/2010 | Annapragada et al. | |
| 7,785,568 B2 | 8/2010 | Annapragada et al. | |
| 8,357,351 B2 | 1/2013 | Karathanasis et al. | |
| 8,642,013 B2 | 2/2014 | Annapragada et al. | |
| 8,679,531 B2 | 3/2014 | Annapragada et al. | |
| 8,911,708 B2 | 12/2014 | Annapragada et al. | |
| 2003/0190284 A1 | 10/2003 | Annapragada et al. | |
| 2006/0099141 A1 | 5/2006 | O'Brien et al. | |
| 2007/0031326 A1 | 2/2007 | Shirvan et al. | |
| 2007/0160658 A1 * | 7/2007 | Connor | A61K 9/1271 424/450 |
| 2007/0292354 A1 * | 12/2007 | Port | A61K 49/1812 424/9.321 |
| 2008/0131369 A1 | 6/2008 | Annapragada et al. | |
| 2009/0123047 A1 | 5/2009 | Yfantis | |
| 2009/0311191 A1 | 12/2009 | Annapragada et al. | |
| 2010/0190831 A1 | 7/2010 | Shi et al. | |
| 2010/0286067 A1 | 10/2010 | Defrees | |
| 2011/0093960 A1 | 4/2011 | Edwards et al. | |
| 2011/0311457 A1 | 12/2011 | Skerrett et al. | |
| 2012/0003159 A1 | 1/2012 | Annapragada et al. | |
| 2012/0258044 A1 | 10/2012 | Annapragada et al. | |
| 2013/0289140 A1 | 10/2013 | Mbebi-Liegeois et al. | |
| 2014/0161875 A1 | 6/2014 | Winderickx et al. | |

FOREIGN PATENT DOCUMENTS

| | | | |
|---|---|---|---|
| EP | 1982733 | | 10/2008 |
| EP | 1982733 A1 | | 10/2008 |
| EP | 2694116 | | 2/2014 |
| WO | 2002028441 | | 4/2002 |
| WO | 0228441 | | 6/2002 |
| WO | 2005107820 | | 11/2005 |
| WO | 2009073236 | | 6/2009 |
| WO | 2009073896 | | 6/2009 |
| WO | 2009150686 | | 12/2009 |
| WO | 2010017094 | | 2/2010 |
| WO | WO-2010-017094 | * | 2/2010 |
| WO | 2010107990 | | 9/2010 |
| WO | 2011045415 | | 4/2011 |
| WO | 2011159297 | | 12/2011 |
| WO | 2011159297 A1 | | 12/2011 |
| WO | 2012119117 | | 9/2012 |
| WO | 2012139080 | | 10/2012 |
| WO | 2013110013 | | 8/2013 |
| WO | 2014152229 | | 9/2014 |
| WO | 2016057812 | | 4/2016 |

OTHER PUBLICATIONS

Klunk W, Imaging AB plaques in living transgenic mice with multiphon microscopy and methoxy-X04, a systemically administered congo red derivative, journal of neuropathology and experimental neurology, 61, 9, 2002, 797-805.*
Ding, et al. "Folate Receptor-targeted Fluorescent Paramagnetic Bimodal Liposomes for Tumor Imaging" Int. J. Nanomedicine, 2011, 6, 2513-2520.
Written opinion and search report from related PCT Application No. PCT/US2012/032649.
Written opinion and search report from related PCT Application No. PCT/US2013/022336.
Winter, PM et al. "Improved Molecular Imaging Contrast Agent for Detection of Human Thrombus" Magnetic Resonance in Medicine, vol. 50, 2003, pp. 411-416; abstract.
Winter, et al., "Improved Molecular Imaging Contrast Agent for Detection of Human Thrombus" Mag. Res. Med. 2003, 50, 411-416.
Thompson, et al., "Cortical Variability and Asymmetry in Normal Aging and Alzheimer's Disease" Cerebral Cortex 1998, 8, 492-509.
McNeely, et al. "Decreased Circulation Time Offsets Increased Efficacy of PEGylated Nanocarriers Targeting Folate Receptors of Glioma" Nanotechnology 2007, 18, 1-11.

(Continued)

*Primary Examiner* — Celeste A Roney
(74) *Attorney, Agent, or Firm* — Benesch Friedlander Coplan & Aronoff LLP; Benjamen E. Kern; Kraig K. Anderson

(57) ABSTRACT

Lipid-based nanoparticle compositions are provided. The compositions generally comprise lipid-hydrophilic polymer-amyloid binding ligand conjugates, and may be liposomal compositions. The compositions, including the liposomal compositions, may be useful for imaging and/or the treatment of amyloid-β plaque deposits characteristic of Alzheimer's Disease.

12 Claims, 13 Drawing Sheets

(56) References Cited

OTHER PUBLICATIONS

Burke, et al., "Imaging of Pulmonary Embolism and t-PA Therapy Effects Using MDCT and Liposomal Iohexol Blood Pool Agent: Preliminary Results in a Rabbit Model" Academic Radial. 2007, 14, 355-362.
Kao, et al., "Long-Residence-Time Nano-Scale Liposomal Iohexol for X-ray-Based Blood Pool Imaging" Acad. Radiol. 2003, 10, 475-483.
Ding, et al., "Folate Receptor-Targeted Fluorescent Paramagnetic Bimodal Liposomes for Tumor Imaging" Int. J. Nanomed. 2011, 6, 2513-2520.
European Search Report issued in EP2756459, dated Jul. 29, 2014
Skaat, et al. "Synthesis of Fluorescent-Maghemite Nanoparticles as Multimodal Imaging Agents for Amyloid-Beta Fibrils Detection and Removal by a Magnetic Field" Biochem. Biophys. Res. Commun. 2009, 386, 645-649.
Van Groen, el al. "Reduction of Alzheimer's Disease Amyloid Plaque Load in Transgenic Mice by D3, a D-Enantiomenc Peptide Identified by Mirror IMage Phage Display" Chem. Med. Chem. 2008, 3, 1848-1852.
Written Opinion and International Search Report from PCT Application No. PCT/US12/032649 dated Jun. 20, 2012.
Mukundan, et al., "A Liposomal Nanoscale Contrast Agent for Preclinical CT in Mice" AJR Am. J. Roentgenol. 2006, 186, 300-307.
Krathanasis, et al., "Multifunctional Nanocarriers for Mammographic Quantification of Tumor Dosing and Prognosis of Breast Cancer Therapy" Biomaterials 2008, 29, 4815-4822.
Karathanasis, et al., "Imaging Nanoprobe for Prediction of Outcome of Nanoparticle Chemotherapy by Using Mammography" Radiology 2009, 250, 398-406.
Karathanasis, et al., "Tumor Vascular Permeability to a Nanoprobe Correlates to Tumor-Specific Expression Levels of Angiogenic Markers" PLoS One 2009, 4, 5843.
Samei, et al., "Micro-CT Imaging of Breast Tumors in Rodents Using a Liposomal, Nanoparticle Contrast Agent" Int. J. Nanomedicine 2009, 4, 277-282.
Klunk, et al., "Imaging AB Plaques in Living Transgenic Mice with Multiphoton Microscopy and Methoxy-XO4, a Systemically Administered Congo Red Derivative" J. Neuropath. Exp. Neurol. 2002, 61, 797-805.
European Search Report in EP2694116, dated Apr. 29, 2015.
Napadow, et al., "Quantitative Analysis of Three-Dimensional-Resolved Fiber Architecture in Heterogeneous Skeletal Muscle Tissue Using NMR and Optical Imaging Methods" Biophys. J. 2001, 80, 2968-2975.
Fosshein, et al., "Paramagnetic Liposomes as MRI Contrast Agents: Influence of Liposomal Physicochemical Properties on the in Vitro Relaxivity" Mag. Res. Imag. 1999, 17, 83-89.
Montez, et al., "Altered temporal correlations in parietal alpha and prefrontal theta oscillations in early-stage Alzheimer Disease" Proceed. Nat. Acad. Sci. 2009, 1-6.
Written Opinion and International Search Report from PCT Application No. PCT/US15/54732 dated Jan. 11, 2016.
Wald, et al., "Spatial Autocorrelation and Mean Intercept Length Analysis of Trabecular Bone Anisotropy Applied to in vivo Magnetic Resonance Imaging" Med. Phys. 2007, 34, 1110-1120.
Written Opinion and International Search Report from PCT Application No. PCT/US13/22336 dated Apr. 1, 2013.
Sellers, "Why Derivatize?", downloaded from http://www.restek.com/pdfs/adv_2007_03_07.

* cited by examiner

LIPID-BASED NANOPARTICLES

CROSS-REFERENCE TO RELATED APPLICATIONS

This application claims priority from U.S. Provisional Patent Application No. 61/472,605, filed on Apr. 6, 2011, which is incorporated by reference herein in its entirety.

STATEMENT REGARDING FEDERALLY SPONSORED RESEARCH OR DEVELOPMENT

This invention was made with Government support under W81XWH-09-2-0139 awarded by the U.S. Department of Defense. The Government has certain rights in this invention.

BACKGROUND

Alzheimer's disease ("AD") is a neurodegenerative illness characterized by memory loss and other cognitive deficits. AD is the most common form of dementia and affects one in every eight people over the age of 65 and one in every two over the age of 85. AD is the sixth leading cause of death in the United States. Over 5.5 million Americans suffer from AD, with an estimated annual cost of $200 billion USD. By 2050, it is projected that AD will affect over 20 million Americans at an annual price tag of $1.1 Trillion USD (in 2011 dollars). Around the world, the estimated figures for the year 2011 were over 37 million sufferers, at an associated cost of over $600 billion (USD).

A significant hindrance to identification and treatment of AD is the paucity of effective diagnostic tests. At present, AD is typically only conclusively diagnosed by post-mortem histopathological analysis. Diagnosis in living patients relies primarily on psychiatric testing to detect cognitive impairment. However, the major neuropathological hallmarks of AD—extracellular amyloid-β ("Aβ") plaque deposits and intracellular neurofibrillary tangles—manifest long before clinical symptoms are discernable. Aβ deposits also represent a major risk factor for hemorrhagic stroke.

Thus, a need exists for compositions and methods suitable for in vivo imaging of intracranial Aβ plaque deposits, for diagnostic purposes and to monitor the effectiveness of therapies targeted at preventing Aβ plaque deposits. Current approaches suffer from one or more of a myriad of drawbacks, including invasiveness, lack of specificity of the imaging agents for Aβ deposits, unsuitable resolution, the inability of the imaging agents to cross the blood-brain barrier ("BBB") effectively, a tendency on the part of the imaging agents to induce an unsuitably high pro-inflammatory response in the vicinity of the Aβ deposits, and unsuitable cytotoxicity. Thus, a further need exists for compositions and methods that are suitable for in vivo imaging of intracranial Aβ plaque deposits, but that do not suffer from one or more of the drawbacks of current approaches. A still further need exists for compositions and methods suitable to treat or aid treatment or prophylaxis of AD.

SUMMARY

In one embodiment, a compound of Formula I, or a pharmaceutically acceptable salt or prodrug thereof, is provided:

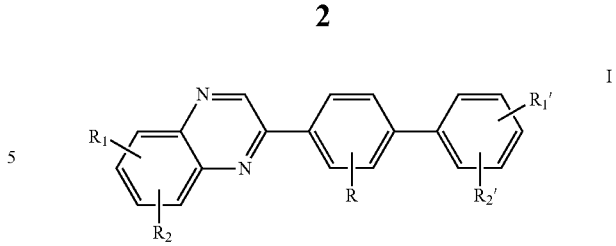

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula I may be conjugated with a hydrophilic polymer, e.g., polyethylene glycol ("PEG") and the like, and a lipid, e.g., 1,2-dipalmitoyl-sn-glycero-3-phosphocholine ("DPPC"), 1,2-distearoyl-sn-glycero-3-phosphoethanolamine ("DSPE"), 1,2-distearoyl-sn-glycero-3-phosphocholine ("DSPC"), 1,2-Dipalmitoyl-sn-glycero-3-phosphoethanolamine ("DPPE"), and the like, to form a lipid-hydrophilic polymer-Formula I ligand conjugate. In one embodiment, the lipid-hydrophilic polymer-Formula I ligand conjugate may be incorporated into a liposomal composition.

In one embodiment, a method for imaging amyloid deposits in a patient is provided, the method comprising:
  introducing into the patient a detectable quantity of a liposomal composition comprising a lipid-hydrophilic polymer-Formula I ligand conjugate;
  allowing sufficient time for the liposomal composition to be associated with one or more amyloid deposits; and
  detecting the liposomal composition associated with the one or more amyloid deposits.

In one embodiment, a compound of Formula II, or a pharmaceutically acceptable salt or prodrug thereof, is provided:

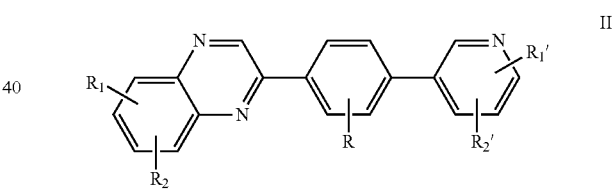

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula II may be conjugated with a hydrophilic polymer, e.g., PEG and the like, and a lipid, e.g., DPPC, DSPE, DSPC, DPPE, and the like, to form a lipid-hydrophilic polymer-Formula II ligand conjugate. In one embodiment, the phospholipid-hydrophilic polymer-Formula II ligand conjugate may be incorporated into a liposomal composition.

In one embodiment, a method for imaging amyloid deposits in a patient is provided, the method comprising:
  introducing into the patient a detectable quantity of a liposomal composition comprising a lipid-hydrophilic polymer-Formula II ligand conjugate;
  allowing sufficient time for the liposomal composition to be associated with one or more amyloid deposits; and
  detecting the liposomal composition associated with the one or more amyloid deposits.

In one embodiment, a compound of Formula III, or a pharmaceutically acceptable salt or prodrug thereof, is provided:

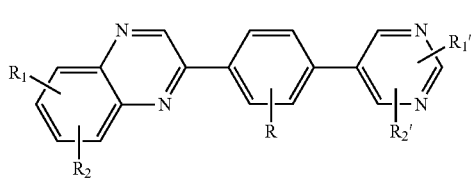

III

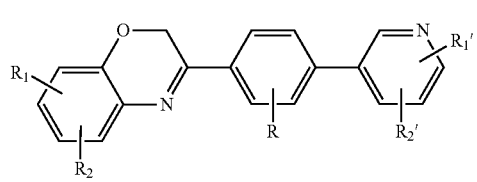

V wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula III may be conjugated with a hydrophilic polymer, e.g., PEG and the like, and a lipid, e.g., DPPC, DSPE, DSPC, DPPE, and the like, to form a lipid-hydrophilic polymer-Formula III ligand conjugate. In one embodiment, the lipid-hydrophilic polymer-Formula III ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula III ligand conjugate;

allowing sufficient time for the liposomal composition to be associated with one or more amyloid deposits; and detecting the liposomal composition associated with the one or more amyloid deposits.

In one embodiment, a compound of Formula IV, or a pharmaceutically acceptable salt or prodrug thereof, is provided:

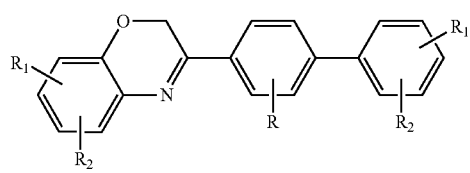

IV wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula IV may be conjugated with a hydrophilic polymer, e.g., PEG and the like, and a lipid, e.g., DPPC, DSPE, DSPC, DPPE, and the like, to form a lipid-hydrophilic polymer-Formula IV ligand conjugate. In one embodiment, the lipid-hydrophilic polymer-Formula IV ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula IV ligand conjugate;

allowing sufficient time for the liposomal composition to be associated with one or more amyloid deposits; and detecting the liposomal composition associated with the one or more amyloid deposits.

In one embodiment, a compound of Formula V, or a pharmaceutically acceptable salt or prodrug thereof, is provided:

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula V may be conjugated with a hydrophilic polymer, e.g., PEG and the like, and a lipid, e.g., DPPC, DSPE, DSPC, DPPE, and the like, to form a lipid-hydrophilic polymer-Formula V ligand conjugate. In one embodiment, the lipid-hydrophilic polymer-Formula V ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula V ligand conjugate;

allowing sufficient time for the liposomal composition to be associated with one or more amyloid deposits; and detecting the liposomal composition associated with the one or more amyloid deposits.

In one embodiment, a compound of Formula VI, or a pharmaceutically acceptable salt or prodrug thereof, is provided:

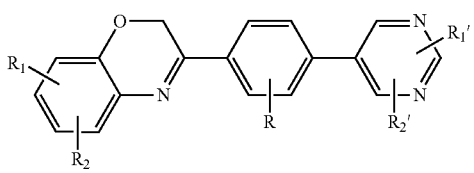

VI wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, the aromatic heterocycle of Formula VI may be conjugated with a hydrophilic polymer, e.g., PEG and the like, and a lipid, e.g., DPPC, DSPE, DSPC, DPPE, and the like, to form a lipid-hydrophilic polymer-Formula VI ligand conjugate. In one embodiment, the lipid-hydrophilic polymer-Formula VI ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula VI ligand conjugate;

allowing sufficient time for the liposomal composition to be associated with one or more amyloid deposits; and detecting the liposomal composition associated with the one or more amyloid deposits.

In one embodiment, a compound of Formula VII, or a pharmaceutically acceptable salt or prodrug thereof, is provided:

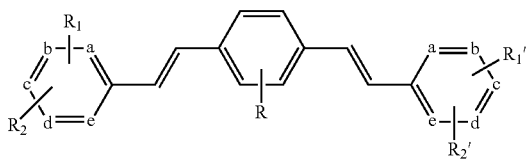

VII wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl; and wherein a, b, c, d, e=C, N, O, or S.

In one embodiment, the aromatic compound of Formula VII may be conjugated with a hydrophilic polymer, e.g., PEG and the like, and a lipid, e.g., DPPC, DSPE, DSPC, DPPE, and the like, to form a lipid-hydrophilic polymer-Formula VII ligand conjugate. In one embodiment, the lipid-hydrophilic polymer-Formula VII ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula VII ligand conjugate;

allowing sufficient time for the liposomal composition to be associated with one or more amyloid deposits; and detecting the liposomal composition associated with the one or more amyloid deposits.

In one embodiment, a liposomal composition is provided, the liposomal composition comprising:

a phospholipid;

cholesterol, or another stabilizing excipient, such as another sterol or a fatty acid;

a nonradioactive gadolinium-containing contrast enhancing agent;

a phospholipid which is derivatized with a polymer; and a conjugate comprising an aromatic compound having any one of Formulas I-VII, such as a conjugate in a form of a lipid-hydrophilic polymer-aromatic conjugate as described herein.

In one embodiment, the liposomal composition comprises:

DPPC;

cholesterol;

(diethylenetriaminepentaacetic acid)-bis(stearylamide), gadolinium salt ("Gd-DTPA-BSA")

1,2-distearoyl-sn-glycero-3-phosphoethanolamine-N-[methoxy(polyethylene glycol)-2000] ("DSPE-mPEG-2000"; CAS No. 147867-65-0); and DSPE-PEG$_n$-methoxy-X04, where n (i.e., the number of ethylene glycol repeating units)=about 10 to about 100, or about 30 to about 60.

In one embodiment, a method for imaging amyloid deposits in a patient is provided, the method comprising:

introducing into the patient a detectable quantity of a liposomal composition comprising a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a lipid-hydrophilic polymer-aromatic compound conjugate as described herein;

allowing sufficient time for the liposomal composition to be associated with one or more amyloid deposits; and detecting the liposomal composition associated with the one or more amyloid deposits.

In one embodiment, the detecting comprises detecting by fluorescence imaging (FI). In another embodiment, the detecting comprises detecting by magnetic resonance imaging (MRI). In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, the detecting comprises detecting by FI. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

BRIEF DESCRIPTION OF THE DRAWINGS

In the accompanying figures, chemical formulas, chemical structures, and experimental data are given that, together with the detailed description provided below, describe example embodiments of the claimed invention.

DETAILED DESCRIPTION

Figure 1:
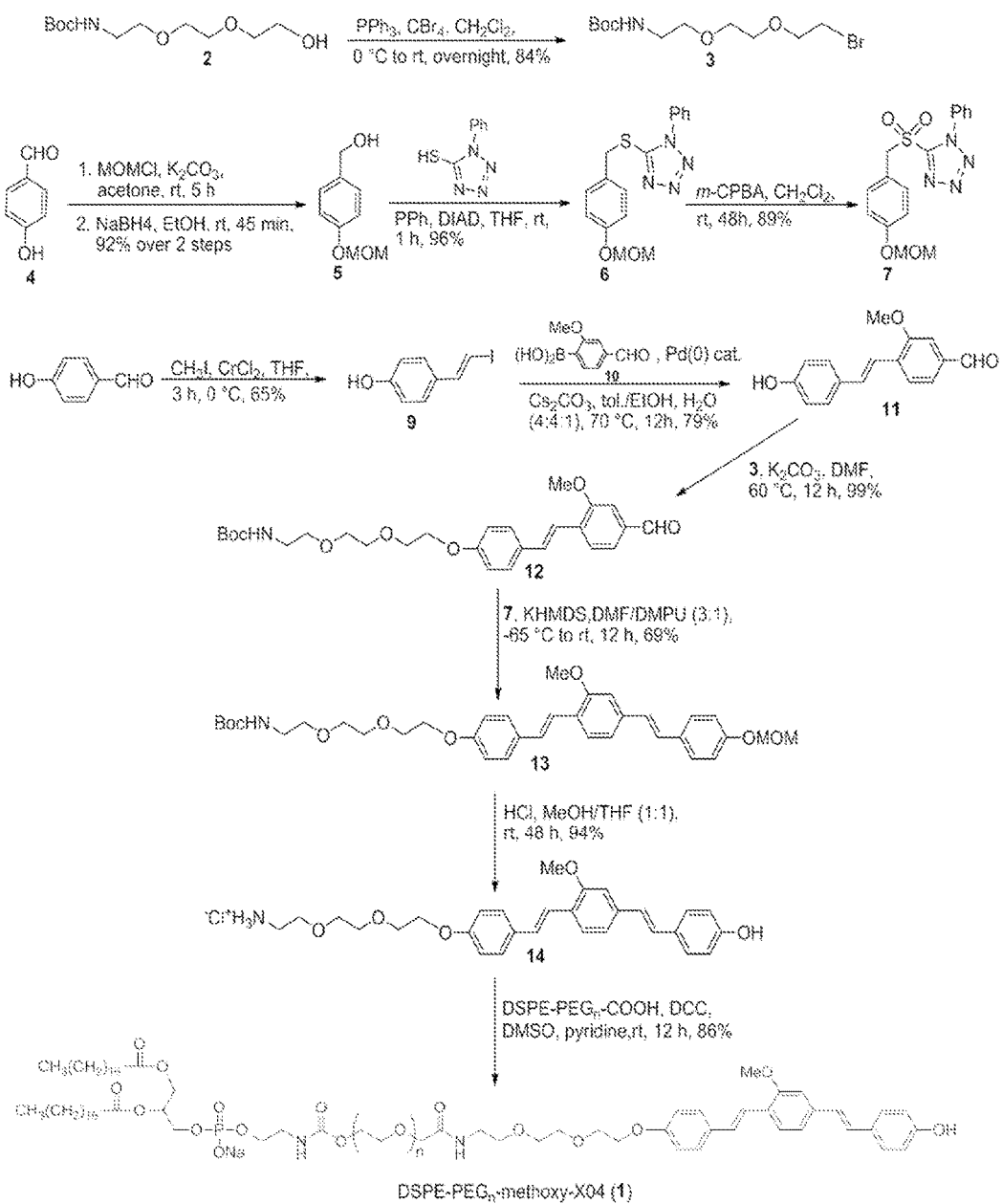
FIG. 1 illustrates an example schematic for the synthesis of the lipid-hydrophilic polymer-aromatic ligand conjugate, DSPE-PEG$_n$-methoxy-XO4 ("Me-XO4").

In one embodiment, a compound of Formula I, or a pharmaceutically acceptable salt or prodrug thereof, is provided:

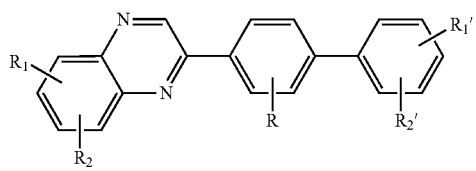

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, and $R_1'$ and $R_2'$ together form the linkage —O—$CH_2$—O— to form a 1,3-benzodioxole. Thus, one example of a compound of Formula I is the 1,4-quinoxaline phenyl 1,3-benzodioxolyl compound IA:

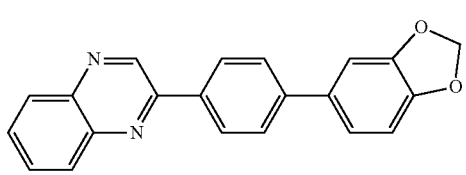

In another embodiment, R=H, $R_1$=H, $R_2$=H, $R_1'$=H, and $R_2'$=$NMe_2$. Thus, another example of a compound of Formula I is the 1,4-quinoxaline biphenyl compound IB:

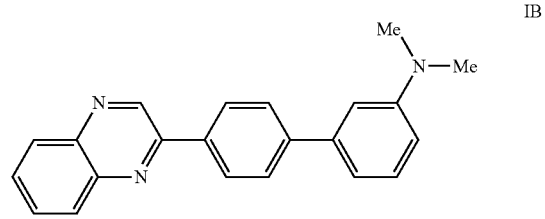 [SMILES: CN(C)c1cccc(-c2ccc(-c3cnc4ccccc4n3)cc2)c1]

In one embodiment, the aromatic heterocycle of Formula I may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula I ligand conjugate.

In one embodiment, the lipid-hydrophilic polymer-Formula I ligand conjugate comprises:

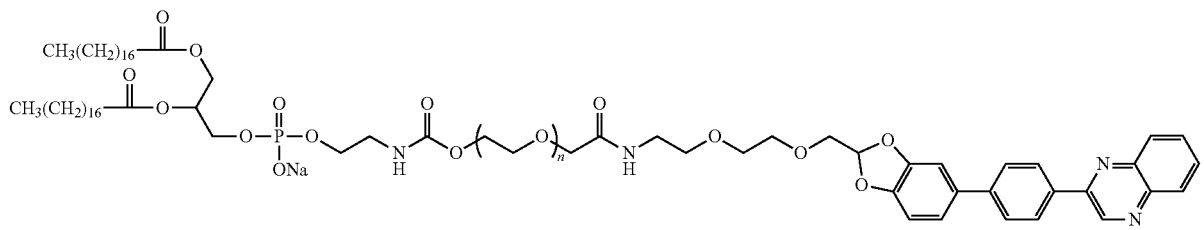

wherein n is about 10 to about 100, or about 30 to about 60.

In another embodiment, the lipid-hydrophilic polymer-Formula I ligand conjugate comprises:

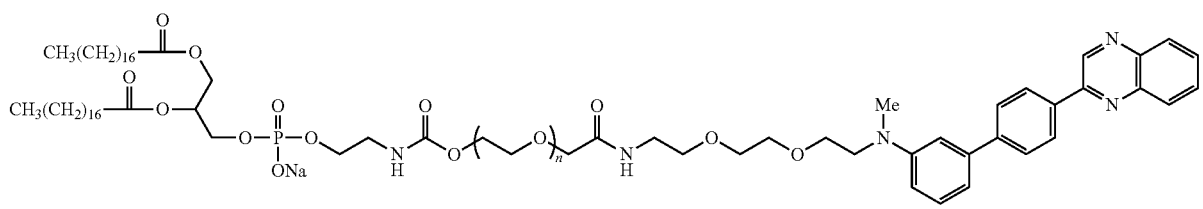

wherein n is about 10 to about 100, or about 30 to about 60.

In one embodiment, the lipid-hydrophilic polymer-Formula I ligand conjugate may be incorporated into a liposomal composition.

In one embodiment, a method for imaging amyloid deposits in a patient is provided, the method comprising:
introducing into the patient a detectable quantity of a liposomal composition comprising a lipid-hydrophilic polymer-Formula I ligand conjugate;
allowing sufficient time for the liposomal composition to be associated with one or more amyloid deposits; and
detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula II, or a pharmaceutically acceptable salt or prodrug thereof, is provided:

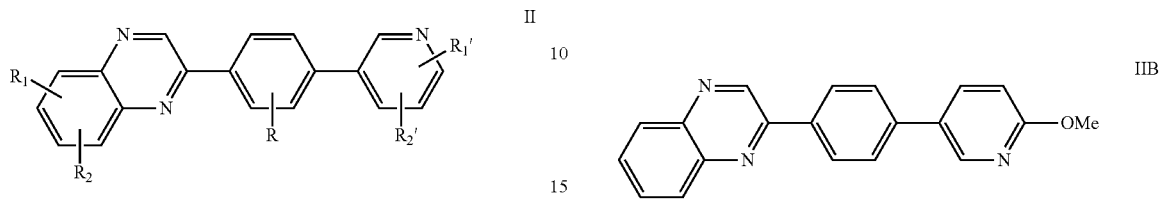

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, $R_1'$=H, and $R_2'$=OMe. Thus, one example of a compound of Formula II is the 1,4-quinoxaline phenyl pyridinyl compound IIA:

Another example of a compound of Formula II is the 1,4-quinoxaline phenyl pyridinyl compound IIB:

In one embodiment, the aromatic heterocycle of Formula II may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula II ligand conjugate.

In one embodiment, the lipid-hydrophilic polymer-Formula II ligand conjugate comprises:

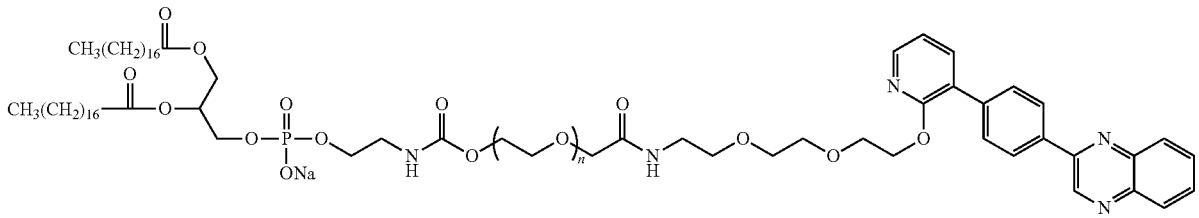

wherein n is about 10 to about 100, or about 30 to about 60.

In another embodiment, the lipid-hydrophilic polymer-Formula II ligand conjugate comprises:

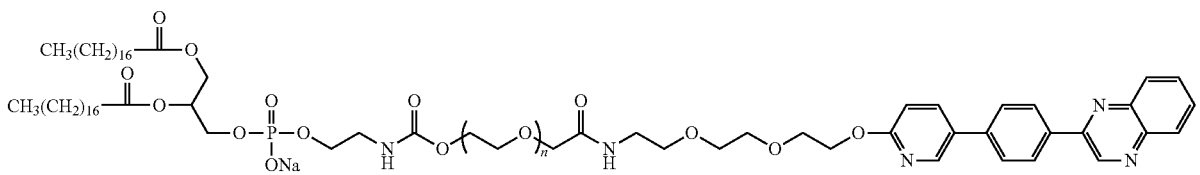

wherein n is about 10 to about 100, or about 30 to about 60.

In one embodiment, the lipid-hydrophilic polymer-Formula II ligand conjugate may be incorporated into a liposomal composition.

In one embodiment, a method for imaging amyloid deposits in a patient is provided, the method comprising:

Da) and the like, and a lipid, e.g., DPPC, DSPE, DSPC, DPPE, and the like, to form a lipid-hydrophilic polymer-Formula III ligand conjugate.

In one embodiment, the lipid-hydrophilic polymer-Formula III ligand conjugate comprises:

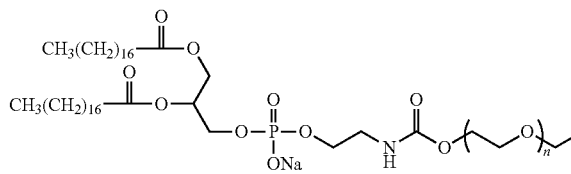

introducing into the patient a detectable quantity of a liposomal composition comprising a lipid-hydrophilic polymer-Formula II ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula III, or a pharmaceutically acceptable salt or prodrug thereof, is provided:

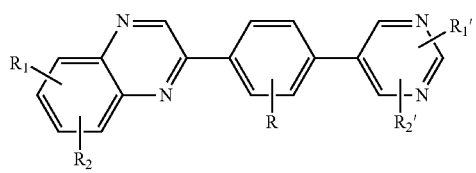

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=H, $R_2$=H, $R_1'$=OMe, and $R_2'$=OMe. Thus, one example of a compound of Formula III is the 1,4-quinoxaline phenyl pyrimidinyl compound IIIA:

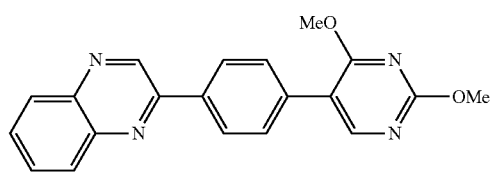

In one embodiment, the aromatic heterocycle of Formula III may be conjugated with a hydrophilic polymer, e.g., PEG (having, e.g., a molecular weight ranging from 500-10,000 wherein n is about 10 to about 100, or about 30 to about 60.

In one embodiment, the lipid-hydrophilic polymer-Formula III ligand conjugate may be incorporated into a liposomal composition.

In one embodiment, a method for imaging amyloid deposit in a patient is provided, the method comprising:

introducing into the patient a detectable quantity of a liposomal composition comprising a lipid-hydrophilic polymer-Formula III ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula IV, or a pharmaceutically acceptable salt or prodrug thereof, is provided:

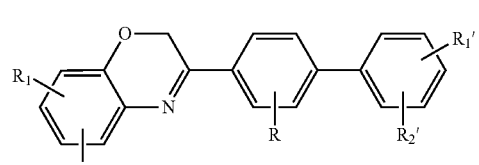

wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=Me, $R_2$=H, and $R_1'$ and $R_2'$ together form the linkage —O—$CH_2$—O— to form a 1,3-benzodioxole. Thus, one example of a compound of Formula IV is the 1,4-benzoxazine phenyl 1,3-benzodioxolyl compound IVA:

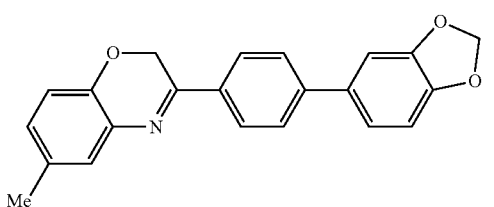

IVA

In another embodiment, R=H, $R_1$=Me, $R_2$=H, $R_1'$=H, and $R_2'$=$NMe_2$. Thus, another example of a compound of Formula IV is the 1,4-benzoxazine biphenyl compound IVB:

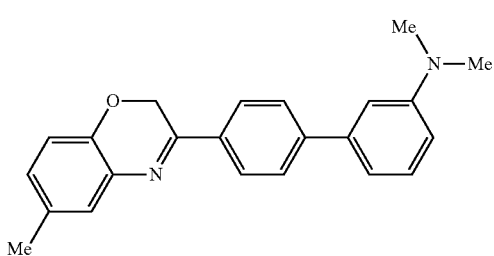

IVB

In one embodiment, the aromatic heterocycle of Formula IV may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula IV ligand conjugate.

In one embodiment, the lipid-hydrophilic polymer-Formula IV ligand conjugate comprises:

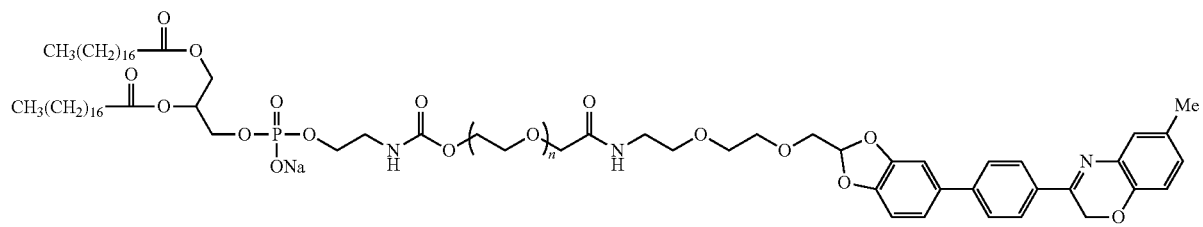

wherein n is about 10 to about 100, or about 30 to about 60.

In another embodiment, the lipid-hydrophilic polymer-Formula IV ligand conjugate comprises:

In one embodiment, the lipid-hydrophilic polymer-Formula IV ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula IV ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula V, or a pharmaceutically acceptable salt or prodrug thereof, is provided:

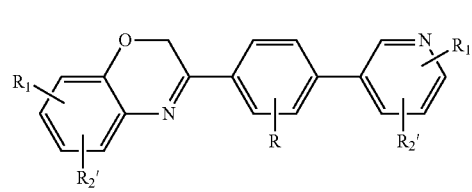

V wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=Me, $R_2$=H, $R_1'$=H, and $R_2'$=OMe. Thus, one example of a compound of Formula V is the 1,4-benzoxazine phenyl pyridinyl compound VA:

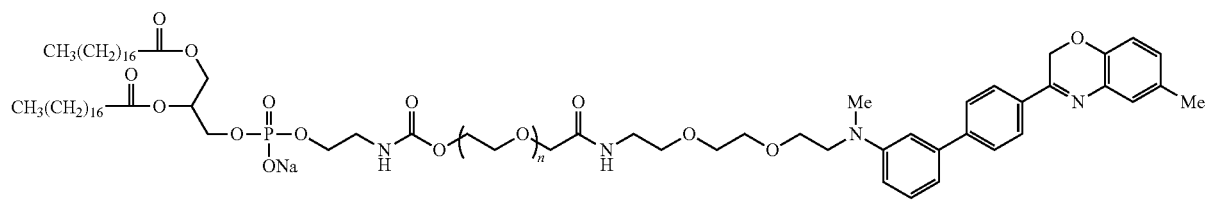

wherein n is about 10 to about 100, or about 30 to about 60.

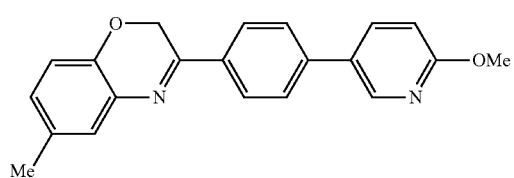

VA

In one embodiment, the aromatic heterocycle of Formula V may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula V ligand conjugate.

In one embodiment, the lipid-hydrophilic polymer-Formula V ligand conjugate comprises:

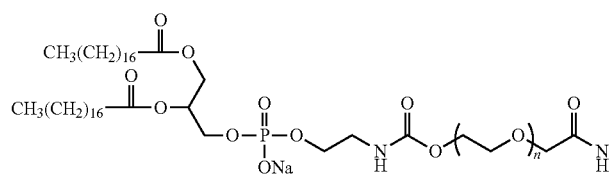

wherein n is about 10 to about 100, or about 30 to about 60.

In one embodiment, the lipid-hydrophilic polymer-Formula V ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula V ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula VI, or a pharmaceutically acceptable salt or prodrug thereof, is provided:

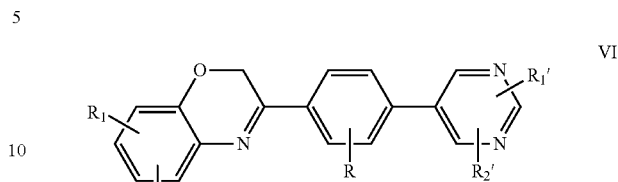

VI wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl.

In one embodiment, R=H, $R_1$=Me, $R_2$=H, $R_1'$=OMe, and $R_2'$=OMe. Thus, one example of a compound of Formula VI is the 1,4-quinoxaline phenyl pyrimidinyl compound VIA:

VIA

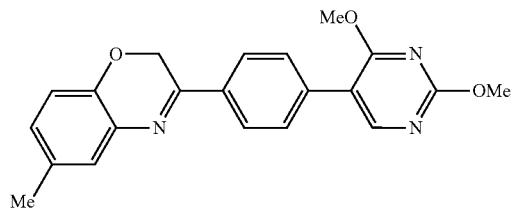

In one embodiment, the aromatic heterocycle of Formula VI may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula VI ligand conjugate.

In one embodiment, the lipid-hydrophilic polymer-Formula VI ligand conjugate comprises:

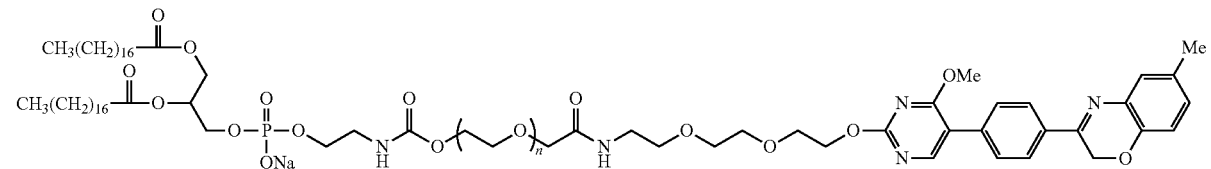

wherein n is about 10 to about 100, or about 30 to about 60.

In one embodiment, the lipid-hydrophilic polymer-Formula VI ligand conjugate may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula VI ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, a compound of Formula VII, or a pharmaceutically acceptable salt or prodrug thereof, is provided:

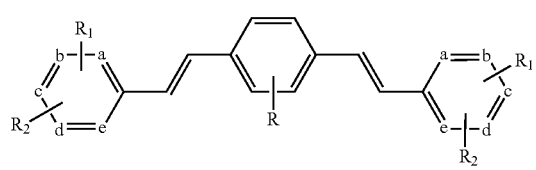

VII wherein R, $R_1$, $R_2$, $R_1'$, $R_2'$=H, F, Cl, Br, I, alkyl, aryl, OH, O-alkyl, O-aryl, $NH_2$, NH-alkyl, N-dialkyl, carboxyl, sulfonyl, carbamoyl, or glycosyl, and a, b, c, d, e=C, N, O, or S.

In one embodiment, R=OMe, $R_1$=H, $R_2$=O-alkyl, $R_1'$=OH, and $R_2'$=H. Thus, one example of a compound of Formula VII is the divinyl benzene compound VIIA ("methoxy-XO4"):

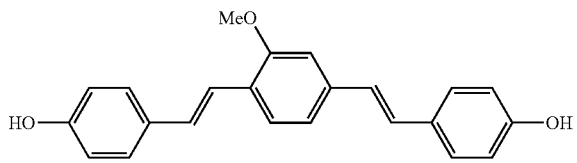

VIIA

In one embodiment, the aromatic compound of Formula VII may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-Formula VII ligand conjugate. For example, in one embodiment, the methoxy-XO4 ligand may be conjugated with PEG and DSPE to form the DSPE-PEG$_n$-Methoxy-XO4 conjugate shown as "1" in FIG. 1 (and sometimes referred to hereinafter as "Me-XO4"):

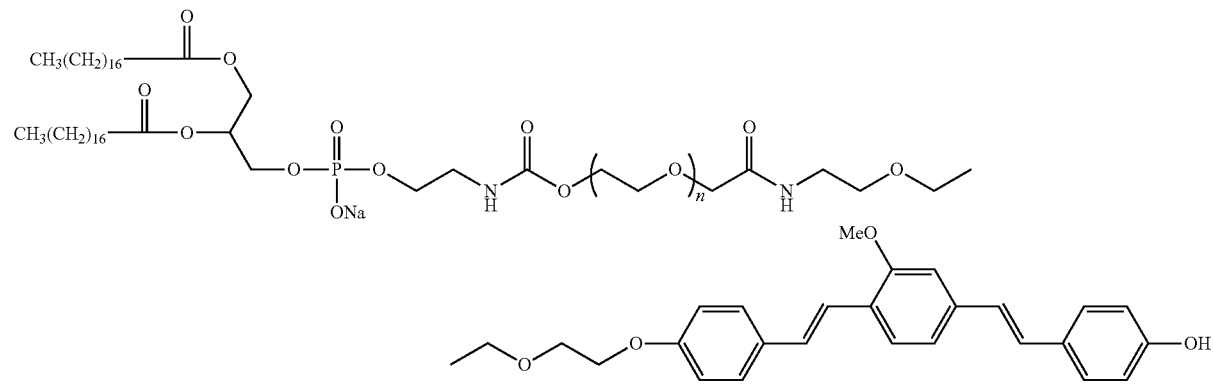

In one embodiment, the lipid-hydrophilic polymer-Formula VII ligand conjugate, e.g., Me-XO4, and even more particularly, DPSE-PEG$_{3400}$-Methoxy-XO4 (where 3400 signifies the molecular weight of the polyethyelene glycol), may be incorporated into a liposomal composition.

In one embodiment, a method for imaging amyloid deposits in a patient is provided, the method comprising:

introducing into the patient a detectable quantity of a liposomal composition comprising a lipid-hydrophilic polymer-Formula VII ligand conjugate;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MR imaging. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

In one embodiment, one or more alternative amyloid ligands (i.e., other than the amyloid binding ligands disclosed above), including, but not limited to, Congo red and its derivatives, Thioflavin T and its derivatives, and CG and its derivatives, may be conjugated with a hydrophilic polymer, e.g., PEG (having, e.g., a molecular weight ranging from 500-10,000 Da) and the like, and a lipid, e.g., DPPC, DSPE, DSPC, DPPE, and the like, to form a lipid-hydrophilic polymer-amyloid ligand conjugate. In one embodiment, the lipid-hydrophilic polymer-amyloid ligand conjugate may be incorporated into a liposomal composition.

In one embodiment, a method for imaging amyloid lesions in a patient is provided, the method comprising:

introducing into the patient a detectable quantity of a liposomal composition comprising a lipid-hydrophilic polymer-amyloid ligand conjugate;

allowing sufficient time for the liposomal composition to be associated with one or more amyloid deposits; and detecting the liposomal composition associated with the one or more amyloid deposits.

The liposomal compositions described herein may further enable delivery of therapeutic molecules to amyloid lesions, thus enabling treatment of the lesions.

In one embodiment, a liposomal composition is provided, the liposomal composition comprising: a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a lipid-hydrophilic polymer-aromatic conjugate as described herein.

In one embodiment, the liposomal composition comprises: DPPC; cholesterol; Gd-DTPA-BSA; DSPE-mPEG-2000; and DSPE-PEG$_n$-methoxy-XO4, where n=about 10 to about 100, or about 30 to about 60.

In one embodiment, a method for imaging amyloid deposits in a patient is provided, the method comprising:

introducing into the patient a detectable quantity of a liposomal composition comprising a phospholipid; cholesterol, or another stabilizing excipient, such as another sterol or a fatty acid; a nonradioactive gadolinium-containing contrast enhancing agent; a phospholipid which is derivatized with a polymer; and a conjugate comprising an aromatic compound having any one of Formulas I-VII, such as a conjugate in a form of a lipid-hydrophilic polymer-aromatic compound conjugate as described herein;

allowing sufficient time for the liposomal composition to be associated with one or more amyloid deposits; and detecting the liposomal composition associated with the one or more amyloid deposits.

In one embodiment, the detecting comprises detecting by FI. In another embodiment, the detecting comprises detecting by MRI. Indeed, hydrophilic paramagnetic chelates such as GdDTPA, GdDOTA, GdHPDO3A, GdDTPA-BMA, and GdDTPA-BSA are known MRI contrast agents. See U.S. Pat. No. 5,676,928 issued to Klaveness et al., which is incorporated by reference herein in its entirety. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD").

Suitable phospholipids may include those disclosed herein, and may further include those disclosed in U.S. Pat. No. 7,785,568 issued to Annapragada et al., which is incorporated by reference herein in its entirety. Suitable polymer derivatized phospholipids may include those disclosed herein, and may further include those disclosed in U.S. Pat. No. 7,785,568.

In one embodiment, the detecting comprises detecting by FI. In one embodiment, the detecting comprises detecting by SPECT imaging and/or PET imaging, and the non-radioactive contrast enhancing agent is replaced with a radioactive contrast enhancing agent, comprising for example those agents deemed appropriate for use with SPECT imaging and/or PET imaging in the National Institute of Health's Molecular Imaging and Contrast Agent Database ("MICAD"). Any other suitable type of imaging methodology known by those skilled in the art is contemplated, including, but not limited to, PET imaging.

EXAMPLES

Certain embodiments are described below in the form of examples. It is impossible to depict every potential application of the invention. Thus, while the embodiments are described in considerable detail, it is not the intention to restrict or in any way limit the scope of the appended claims to such detail, or to any particular embodiment.

Example 1: Preparation of
DSPE-PEG$_{3400}$-Methoxy-XO4 Conjugate 1

The DSPE-PEG$_{MW=3400}$-Methoxy-XO4 conjugate, 1, was synthesized as the targeting species (FIG. 1) and later incorporated into liposomal formulations.

Referring to FIG. 1, the synthesis of compound 14, the linker-methoxy-XO4 moiety, was achieved via a series of Takai, Suzuki, and Julia-Kocienski olefination reactions. The Boc-protected 3-unit PEG linker precursor bromide 3 was prepared from the corresponding commercially available alcohol 2 in good yield. Intermediate 7, the sulfone for the Julia-Kocienski olefination step was also prepared in excellent yields from 4-hydroxybenzaldehyde. 4-hydroxybenzaldehyde was also separately subjected to the standard Takai protocol to afford vinyl iodide 9. Reaction of 9 with commercially available boronic acid 10 under Suzuki conditions afforded compound 11 in good yield. The linker moiety was installed quantitatively to give aldehyde 12, which was exposed to sulfone 7 under optimized Julia-Kocienski conditions to obtain the desired E,E-isomer 13 in 69% yield after column chromatography purification. Global deprotection of the MOM and Boc groups with HCl gave the linker-methoxy-XO4 moiety 14, as the hydrochloride salt.

Conjugation to the lipid-PEG moiety proceeded by subjecting 14 and DSPE-PEG$_{MW=3400}$-COOH to standard carbodiimide conditions to afford the DSPE-PEG$_{MW=3400}$-MeX04 conjugate 1 (a subset of Me-X04).

Figure 1A:
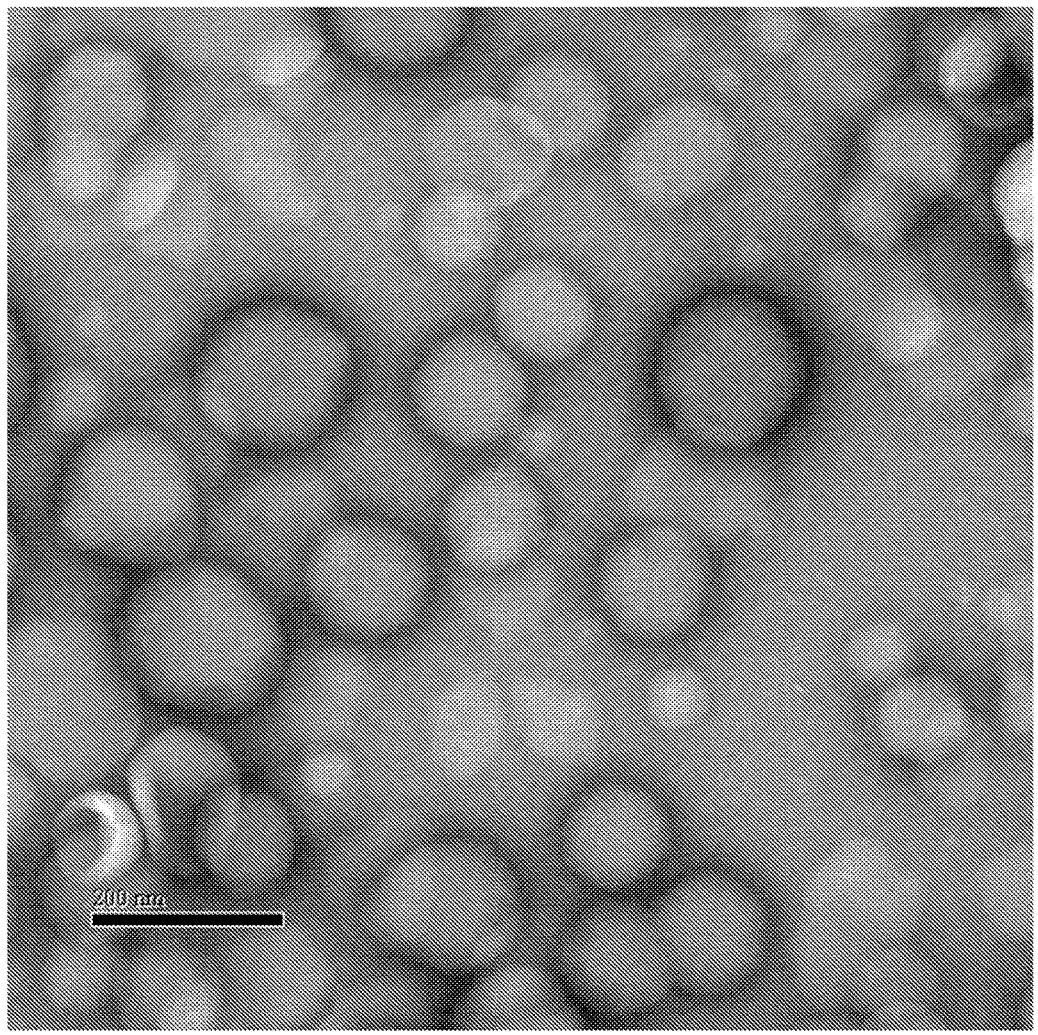
FIG. 1A illustrates example transmission electron microscope ("TEM") images of liposomal DSPE-PEG$_{MW=3400}$-methoxy-XO4.
Figure 1B:
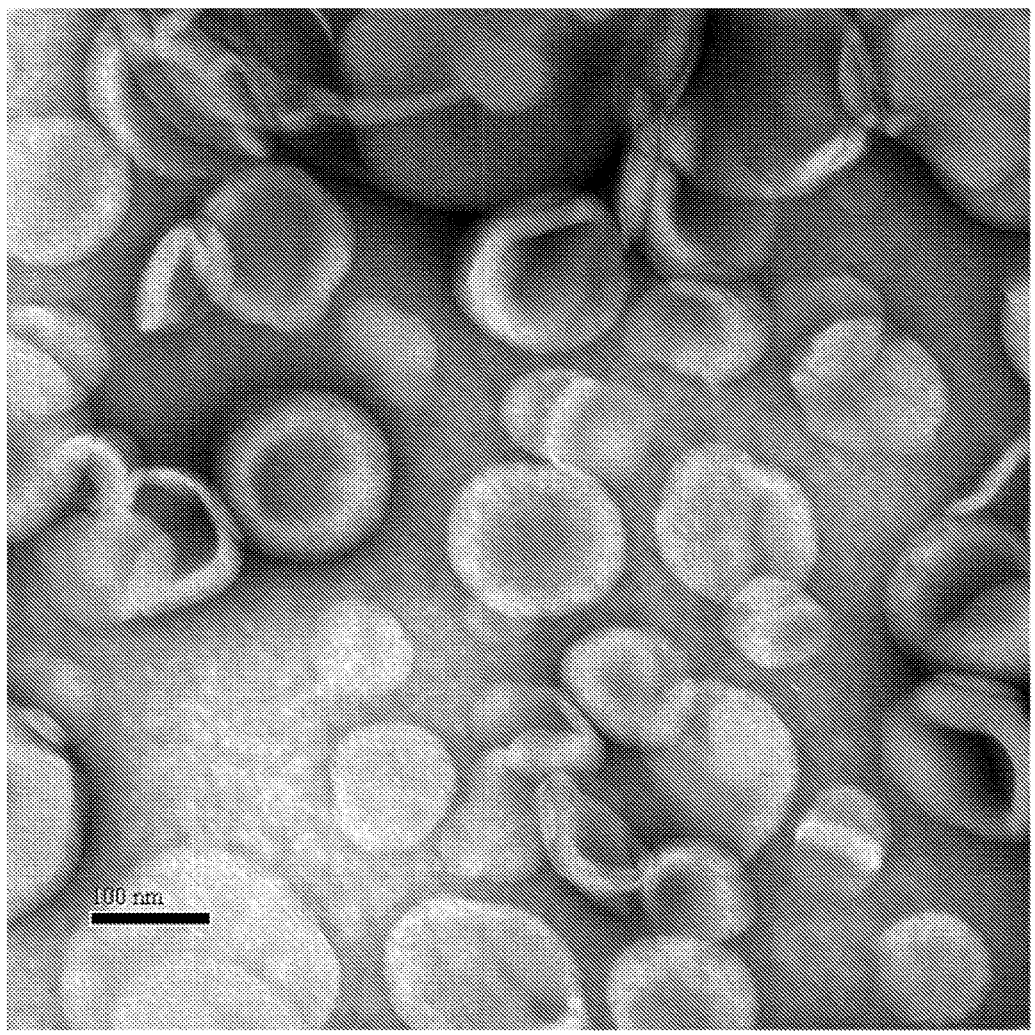
FIG. 1B illustrates further example TEM images of liposomal DSPE-PEG$_{MW=3400}$-methoxy-XO4.

Example 2: Preparation and Characterization of Gd-Containing Me-XO4-Labeled Liposomes A lipid mixture (50 mM) comprising DPPC, cholesterol, Gd-DTPA-BSA, DSPE-mPEG-2000, Me-XO4, and Rhodamine-DHPE (for optical detection) in about a 32.4:40:25:2:0.5:0.1 molar ratio, respectively, was employed. Other ratios are contemplated, including a lipid mixture comprising DPPC, cholesterol, Gd-DTPA-BSA, DSPE-mPEG-2000, and Me-XO4 in about a 32.5:40:25:2:0.5 molar ratio. Additionally, the DSPE-mPEG-2000 may be replaced altogether with the Me-XO4 conjugate, for a DPPC, cholesterol, Gd-DTPA-BSA, Me-XO4 conjugate ratio of 32.5:40:25:2.5. The upper limit on the PEG-bearing molecule may be about 15-25%, and the lower limit on cholesterol may be about 15-20%. Upon hydration in PROHANCE® solution (Bracco Diagnostics, Inc., Monroe Township, N.J.) for 1.5 h, the mixture was sequentially extruded, at 65° C., on a LIPEX™ THERMOLINE EXTRUDER (Northern Lipids Inc., Burnaby, B.C. Canada) with five passes through a 200 nm NUCLEPORE™ membrane (Sigma-Aldrich, St. Louis, Mo.) and ten passes through a 100 nm membrane. Particle size distribution was determined by TEM (FIGS. 1A and 1B), thereby confirming a mean diameter of about 100.8 nm and PDI of about 0.05.

The concentration of Me-XO4 ligand in the particles was determined using a fluorescence standard curve generated for Me-XO4 ligand to be 26 µM. The above protocol results in roughly equal distribution of the targeting ligand between the inner and the outer faces of the lipid bilayer. This implies that for each reported concentration of Me-XO4 ligand in the nanoparticles, approximately 50% of the total Me-XO4 ligands are available for binding. Me-XO4 ligand is highly intrinsically fluorescent and so are the nanoparticles bearing Me-XO4 ligand. This property was used as a reporter on the locations of nanoparticles in the course of all of the experiments.

Example 3: In Vitro Binding Affinity of Gd-Containing Me-XO4-Labeled Liposomes for Synthetic AD Fibrils The Me-XO4-labeled liposomes of Example 2 and Me-XO4 ligand stock solutions were diluted with 10 mM Tris-HCl, pH 7.4, to 500 nM. A small volume of the 100 µM Aβ stock solution was added to the test compounds to achieve a final fibril concentration of 20 µM. This was followed by addition of appropriate concentrations of the non-fluorescent competitor, CG. The binding mixture was incubated at RT for 1 h and then centrifuged for 20 min at 16,400 rpm to separate the fibrils. The precipitate was washed twice with tris-HCl. The fluorescence was measured in a SpectraMax 384 plate (Molecular Devices, Inc. Sunnyvale, Calif.) reader, using excitation and emission wavelengths of 368 nm and 450 nm, respectively.

Figure 2A:
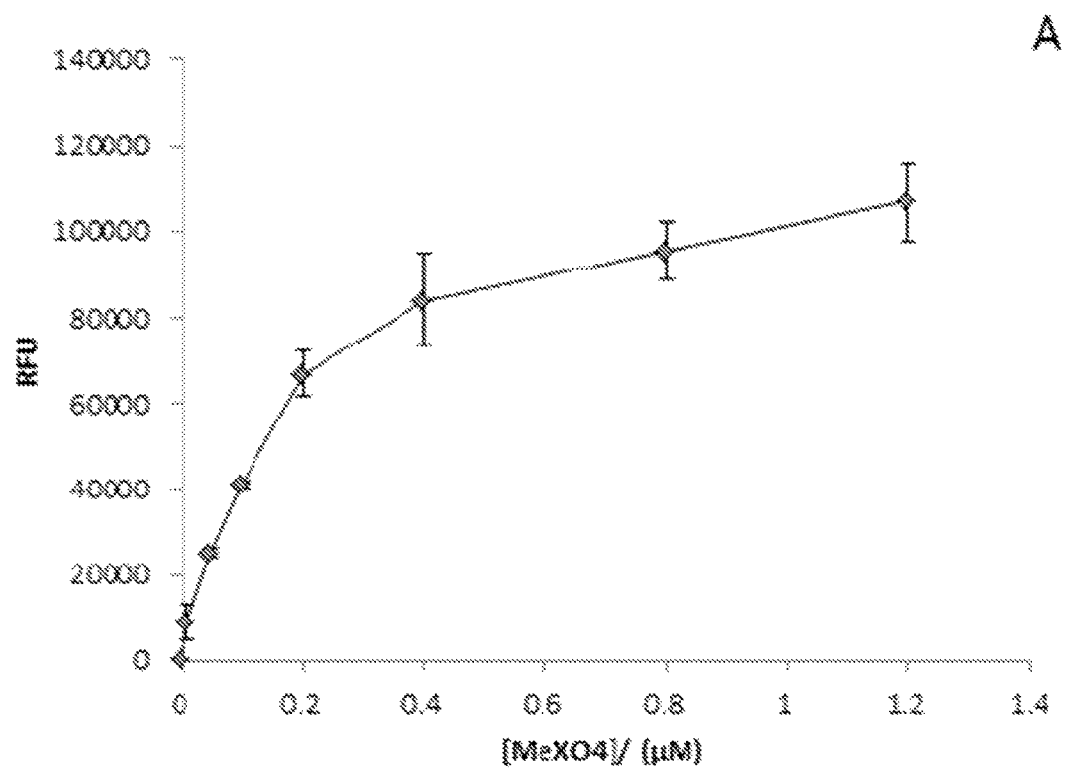
FIG. 2A illustrates the binding affinity of Me-XO4-labeled liposomes to synthetic Aβ(1-40) fibrils.
Figure 2B:
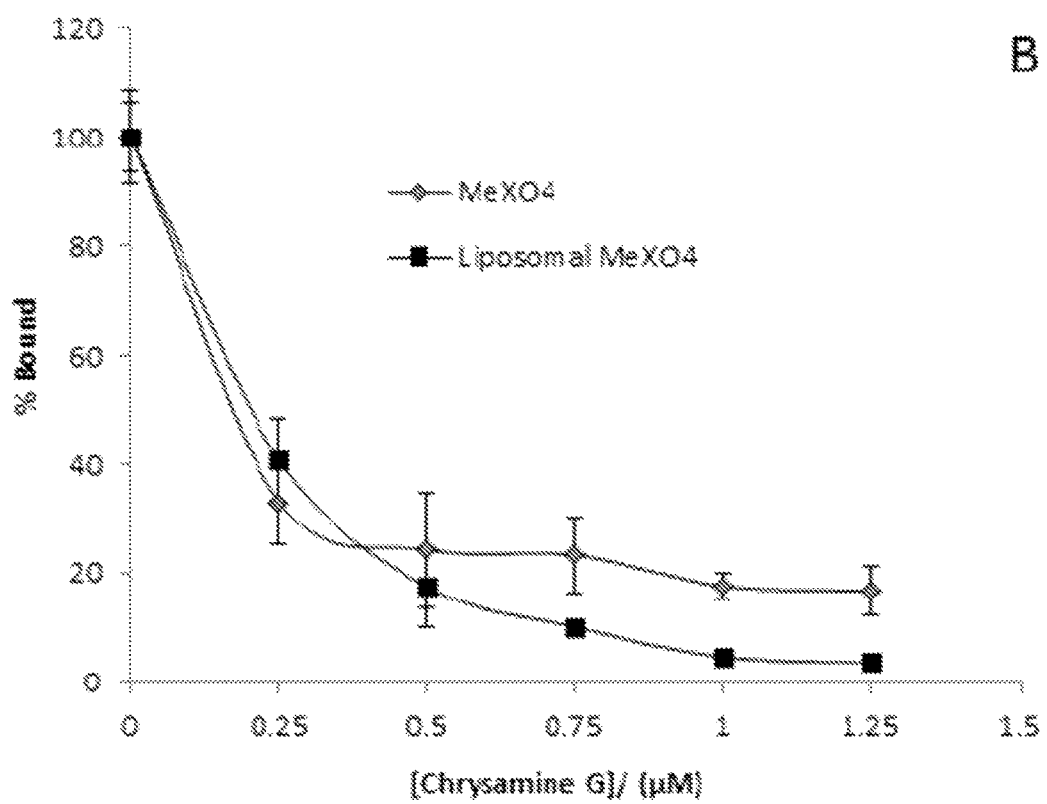
FIG. 2B illustrates example results of the competition between Me-XO4-labeled liposomes, Chrysamine G ("CG"), and free methoxy-XO4 ligand, for binding sites on synthetic Aβ(1-40) fibrils.

FIG. 2A illustrates the binding affinity of the Gd-containing Me-XO4-labeled liposomes of Example 2 to synthetic Aβ(1-40) aggregates. FIG. 2B illustrates the ability of Gd-containing Me-XO4-labeled liposomes to compete for binding sites with free Me-XO4 ligand.

Example 4: Ex Vivo Staining of Mouse Brain Tissue

The ability of the Gd-containing Me-XO4-labeled liposomes of Example 2 to bind Aβ plaques was assessed by staining brain sections from APP/PSEN1 transgenic mouse line. The mice were engineered to progressively develop cortical and hippocampal Aβ plaques in an age-related manner similar to that observed in human AD pathology. Saggital sections (30 µm thick) from euthanized non-transgenic (control), 5, and 7 month old APP/PSEN1 mice were incubated in a 3 mM solution of the liposomes (concentration of Me-XO4 in the solution was 1 µM) for 2 h, at RT. This was followed by extensive washing with PBS to remove unbound liposomes. The stained tissues were mounted with VECTASHIELD® mounting media (Vector Laboratories, Inc., Burlingame, Calif.) to reduce background fluorescence and viewed under a confocal microscope.

Figure 3:
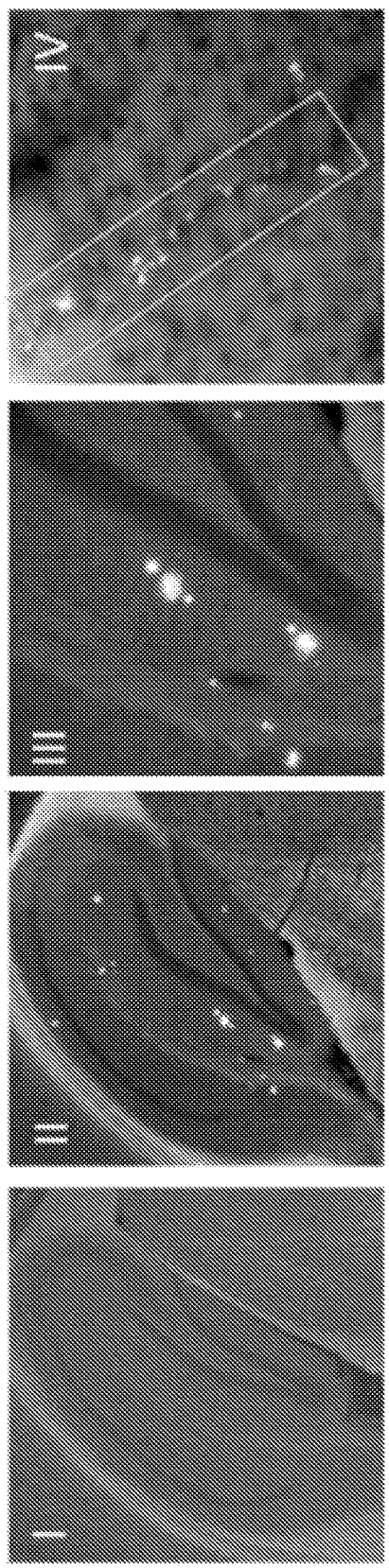
FIG. 3 illustrates example results of ex vivo staining of mouse brain tissue with Me-XO4-labeled liposomes.

As shown in FIG. 3, slides from the non-transgenic mice (panel I) showed no distinct fluorescent spots due to the absence of plaques. Distinct plaque deposits (panels II and III) as well as cerebral amyloid angiopathy (panel IV) were highlighted by the agent on brain sections from the 7 month old mice, but not the 5 months old mice. The same plaque deposition pattern was observed when similar sections were subjected to the same protocol with free methoxy-XO4 ligand.

Figure 4:
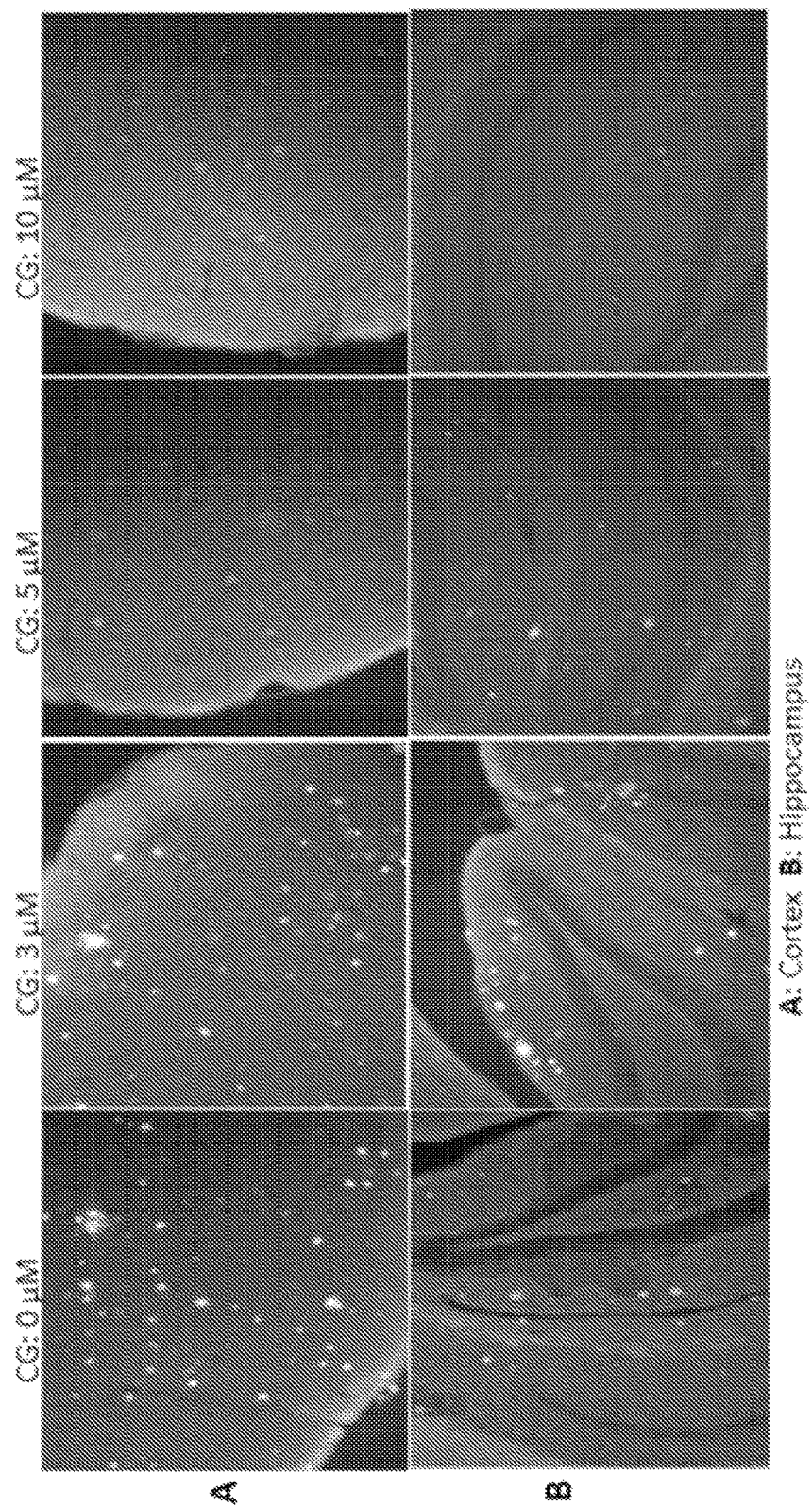
FIG. 4 illustrates example results of the competition between Me-XO4-labeled liposomes and CG for binding sites on Aβ plaque deposits on mouse brain tissue, ex vivo.

To further confirm the ability of the Gd-containing Me-XO4-labeled liposomes to selectively bind Aβ plaque deposits in brain tissue, the staining protocol was repeated with 1 µM Me-XO4 and increasing concentrations of CG. The results (FIG. 4) show a decrease in fluorescence intensity and the number of labeled plaques in both the cortex (A) and hippocampus (B), with increasing CG concentration.

Example 5: In Vivo Delivery of Gd-Containing Me-XO4-Labeled Liposomes to Cortical and Hippocampal Plaques in a 7 Month Old APP/PSEN1 Transgenic Mouse Line The Gd-containing Me-XO4-labeled liposomes were administered to 5 and 7 month old APP/PSEN1 mice by tail vain injection. 48 h following injection, the mice were euthanized and their brains sectioned for confocal light microscopic studies. Identical mice were injected with molecular/free methoxy-XO4 ligand to serve as a positive control, and with untargeted liposomes and saline as negative controls.

Figure 5:
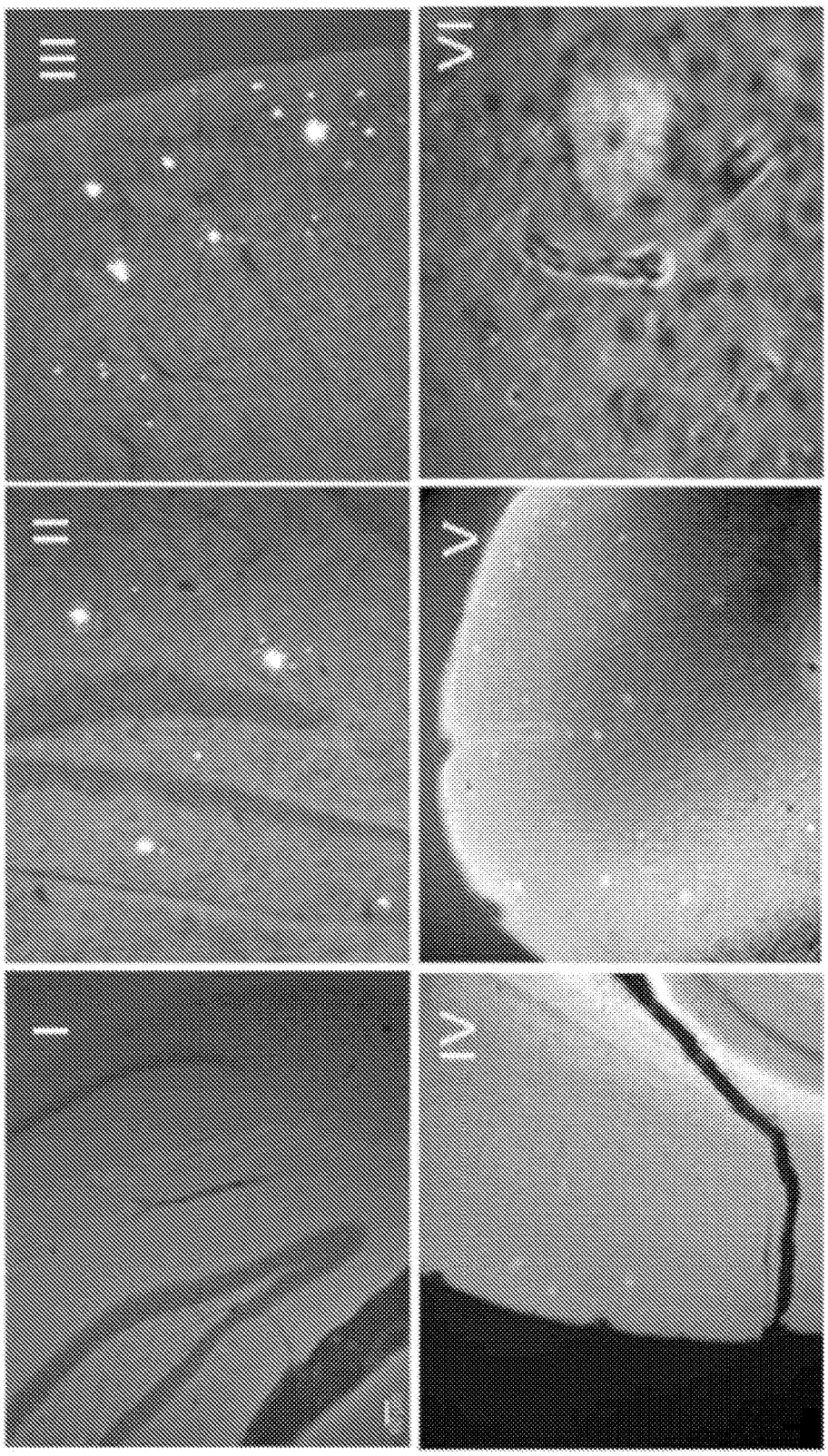
FIG. 5 illustrates example results of in vivo staining of mouse brain tissue with Me-XO4-labeled liposomes, and with free methoxy-XO4 ligand.

There was no noteworthy fluorescence (indicating the absence of plaques) when brain tissue sections from any of the 5 month old mice were imaged. Sections from the 7 month old mice (FIG. 5) injected with untargeted liposomes (panel I) and saline showed no fluorescence as well. Identical mice injected with free methoxy-XO4 ligand (panels II and III) revealed bright staining of both cortical and hippocampal plaques. Animals injected with Gd-containing Me-XO4 liposomes (panels IV, V, and VI) revealed similar plaque deposits and vascular pathology.

Figure 6:
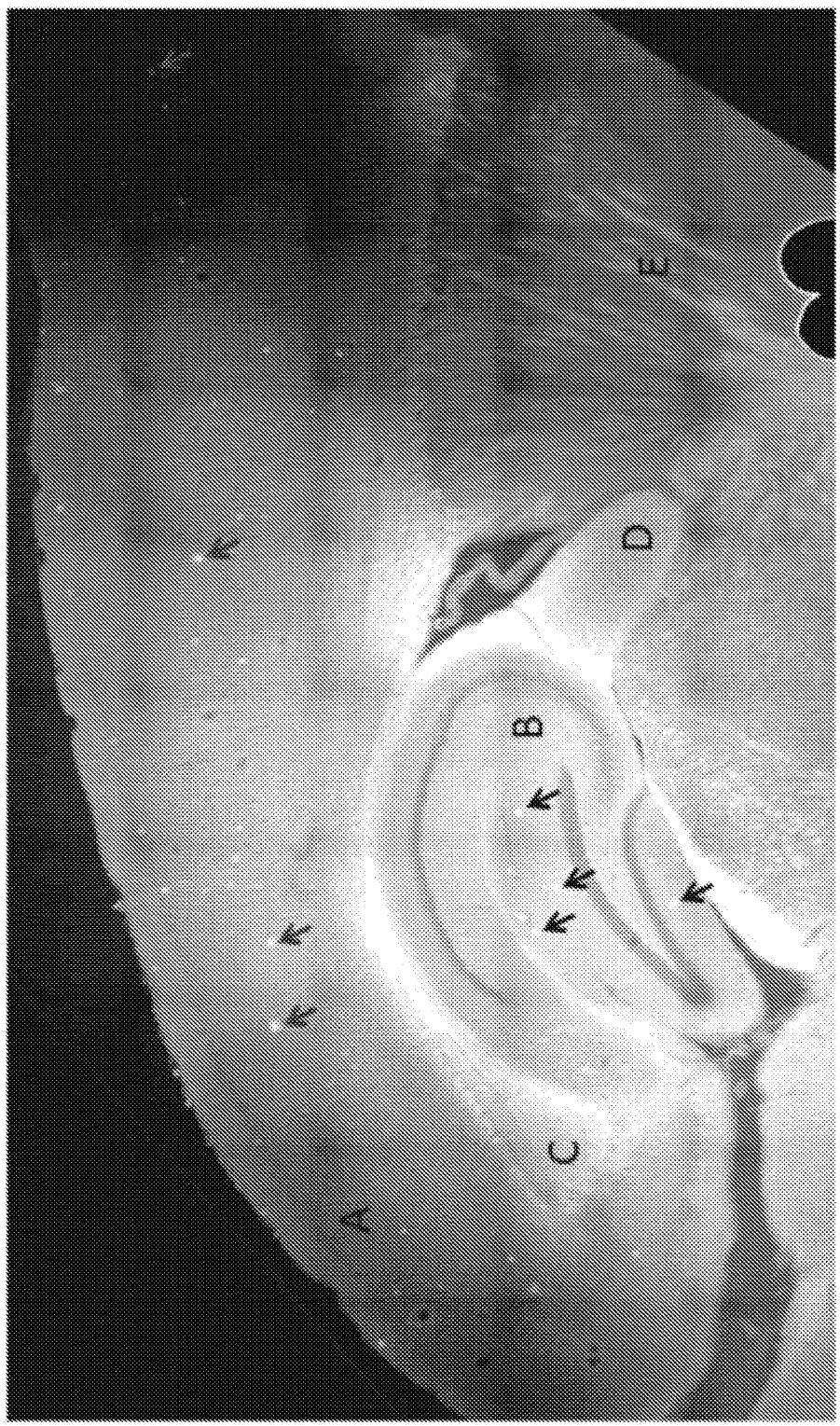
FIG. 6 illustrates an optical reconstruction of example confocal microscope images from a sagittal section of a mouse brain injected with Me-XO4-labeled liposomes.

Optical reconstruction of images on a slide from one of the nanoparticle treated mice in this study (FIG. 6) show localization of fluorescence predominantly in the cortex (top-most four arrows, in section A) and hippocampus (bottom-most four arrows, in section B). The Gd-containing Me-XO4 liposomes penetrated the BBB barrier and pervasively migrated through the brain.

Example 6: Inflammatory Potential of Me-XO4

Inflammation around the amyloid deposit is considered to be a major risk factor for the progression of AD. Thus, it is highly desirable for imaging agents to present a low or reduced inflammation risk. Lipid-PEG-ligand conjugates generally tend to be inflammatory in nature. Indeed, lipopolysaccharides ("LPS"), which are similar to lipid-PEG-ligand conjugates in structure, are among the most inflammatory compositions known.

The inflammatory potential of Me-XO4 was compared to free (i.e., unconjugated) methoxy-XO4 ligand, LPS, and an untreated control ("UTC"). Translocation of NF-kb from cytosol to the nucleus is an early event in the inflammatory reaction. Upon receiving the inflammatory potential, NF-kb moves from the cytoplasm to the nucleus and induces gene transcription. Therefore translocation of NF-kB is a widely used marker for inflammation. In brief, the protocol is outlined below.

15,000 HeLa cells were plated in each of 96 well plates and allowed to stand overnight. The cells were treated with the different concentrations of the test compounds for 2 h in a 37° C. incubator. The positive controls were treated with 1 mg/mL LPS. At the end of the incubation period, the medium was aspirated and the cells were washed with PBS. The cells were treated with 4% paraformaldehyde (to fix the cells) for 10 min at RT. The cells were washed twice with ice cold PBS. The cells were incubated with 0.25% Triton-X-100 in PBS for 10 min at RT, and were again washed three times (5 min each wash) with PBS. The cells were incubated with 1% BSA in PBS-T (PBS with 0.1% Tween-20) for 45 min at RT. At the end of the incubation period, the cells were further incubated with primary antibody against NF-kB at 1:50 dilution in PBST for 1 h at RT. The cells were again washed with PBS three times (5 min each). The cells were incubated with the secondary antibody in PBST for 1 h at RT, and were again washed three times (5 min each) with PBS. 100 µl of DAPI (1 µg/mL) was placed in each well and kept at 4° C. until further analysis. The cells were scanned on a Cell Lab IC-100 image cytometer (Beckman-Coulter, Fullerton, Calif.). The data were further analyzed using CyteSeer software (Vala Sciences, San Diego, Calif.), and represented as Pearson's Correlation coefficient (PCC) of the protein intensity present over the nuclear mask.

Figure 7:
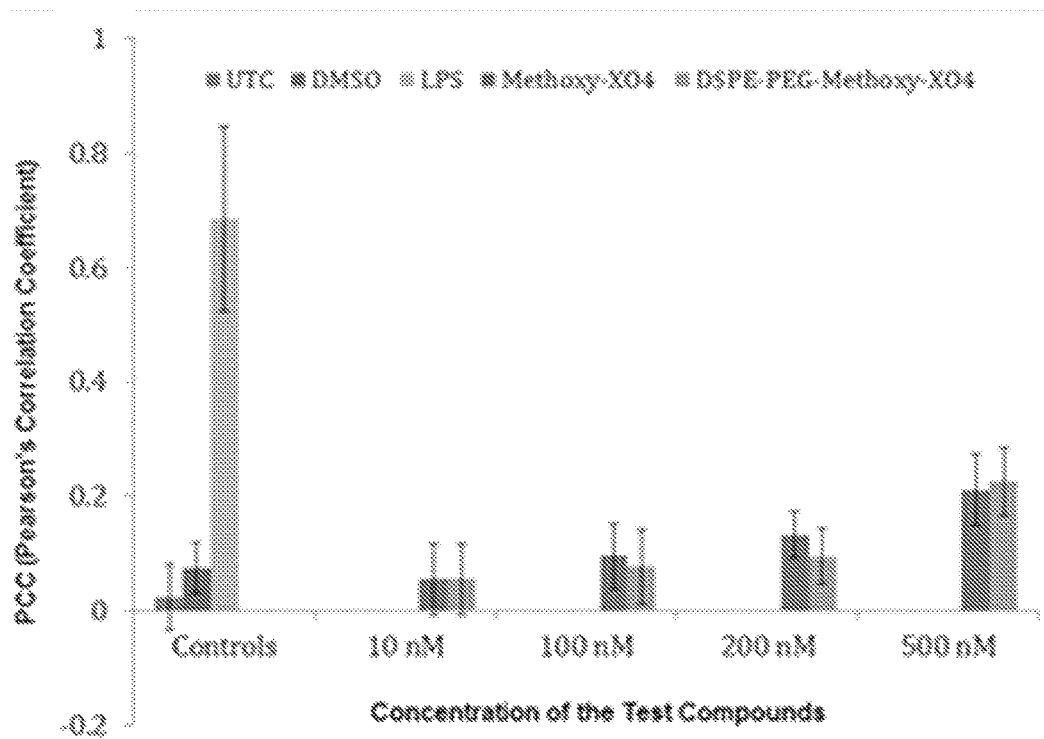
FIG. 7 illustrates an example comparison of inflammatory potential between free methoxy-XO4 ligand and the Me-XO4 conjugate.

Surprisingly, Me-XO4 was found to be less inflammatory than free methoxy-XO4 ligand at all but the highest concentrations (500 nM) tested. The results are depicted in FIG. 7.

Thus, it is a particular teaching of at least one embodiment herein that the conjugated and/or liposomal amyloid binding ligand is less (or at least not more) inflammatory than the free ligand.

Example 7: Cytotoxicity of Me-XO4

The cytotoxicity of Me-XO4 was compared to free (i.e., not conjugated) methoxy-XO4 ligand and an untreated control. The toxicity of the test compounds was evaluated using standard MTT assays. 15,000 HeLa cells were plated in each of 96 well plates and allowed to stand overnight. The cells were treated with three different concentrations of the test compounds for 2 h in a 37° C. incubator. The positive controls were treated with 1 mg/mL LPS. At the end of the incubation period, a MTS cell toxicity assay kit (CELLTITER 96® AQueous Assay kit, Promega, Madison Wis.) was used according to the manufacturer's protocol. At the end of the incubation period, cells were treated with 15 µL MTS reagent/100 µL media for 3 h at 37° C. After 3 h of incubation, the absorbance was recorded at 490 nm using a plate reader.

Figure 8:
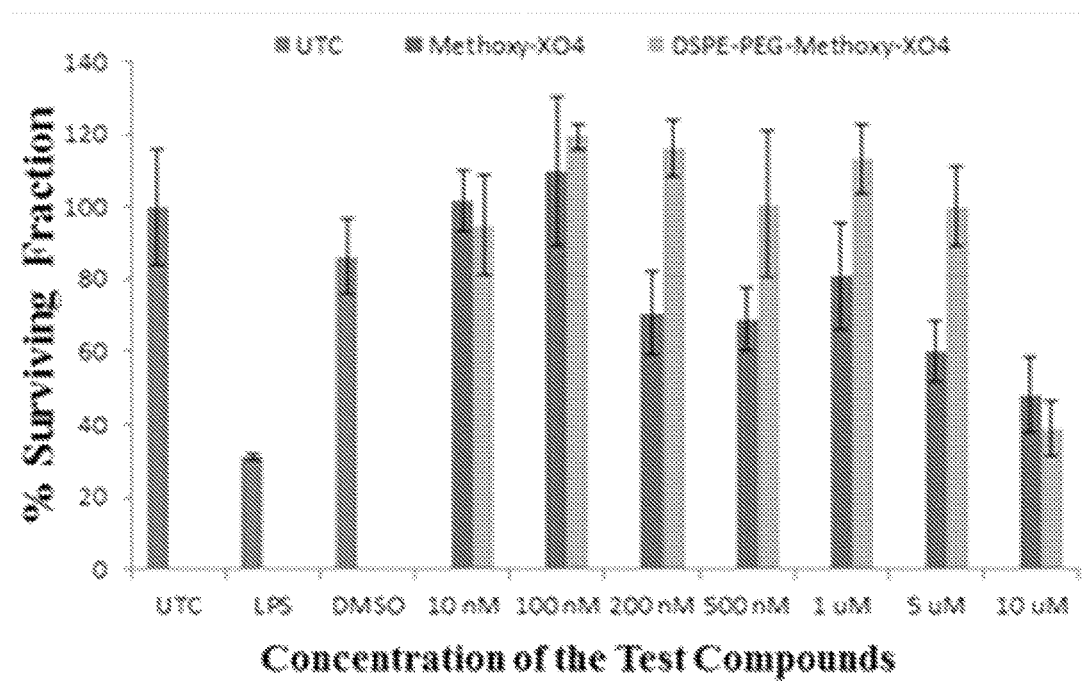
FIG. 8 illustrates an example comparison of cellular toxicity between free methoxy-XO4 ligand and the Me-XO4 conjugate.

Surprisingly, Me-XO4 was found to be less cytotoxic than free methoxy-XO4 ligand. The results are depicted in FIG. 8. Thus, it is a particular teaching of at least one embodiment herein that the conjugated and/or liposomal amyloid binding ligand is less (or at least not more) toxic than the free ligand.

Figure 9A:
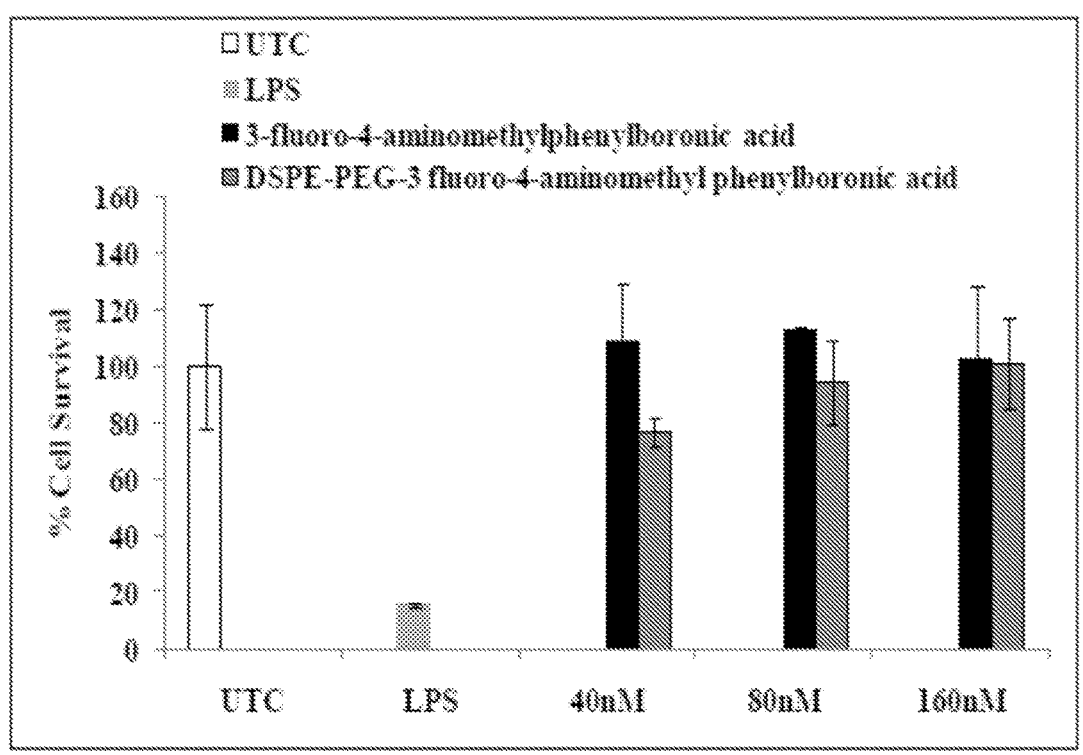
FIG. 9A illustrates a comparison of cellular toxicity between DSPE-PEG-3-fluoro-4-aminomethylphenyl boronic acid conjugate and the free ligand, 3-fluoro-4-aminomethylphenyl boronic acid.

(Comparative) Example 8: Cytotoxicity and Inflammatory Potential of Boronic Acid Ligand Upon Conjugation to a Lipid-PEG Anchor The cytotoxicity of 3-fluoro-4-aminomethylphenylboronic acid was compared to the conjugated ligand, namely DSPE-PEG-3-fluoro-4-aminomethylphenylboronic acid, LPS, and an untreated control, according to the same protocols as described above in Example 7. FIG. 9A illustrates the surviving fraction of cells. As expected, the conjugated ligand is significantly more cytotoxic than the free ligand.

Figure 9B:
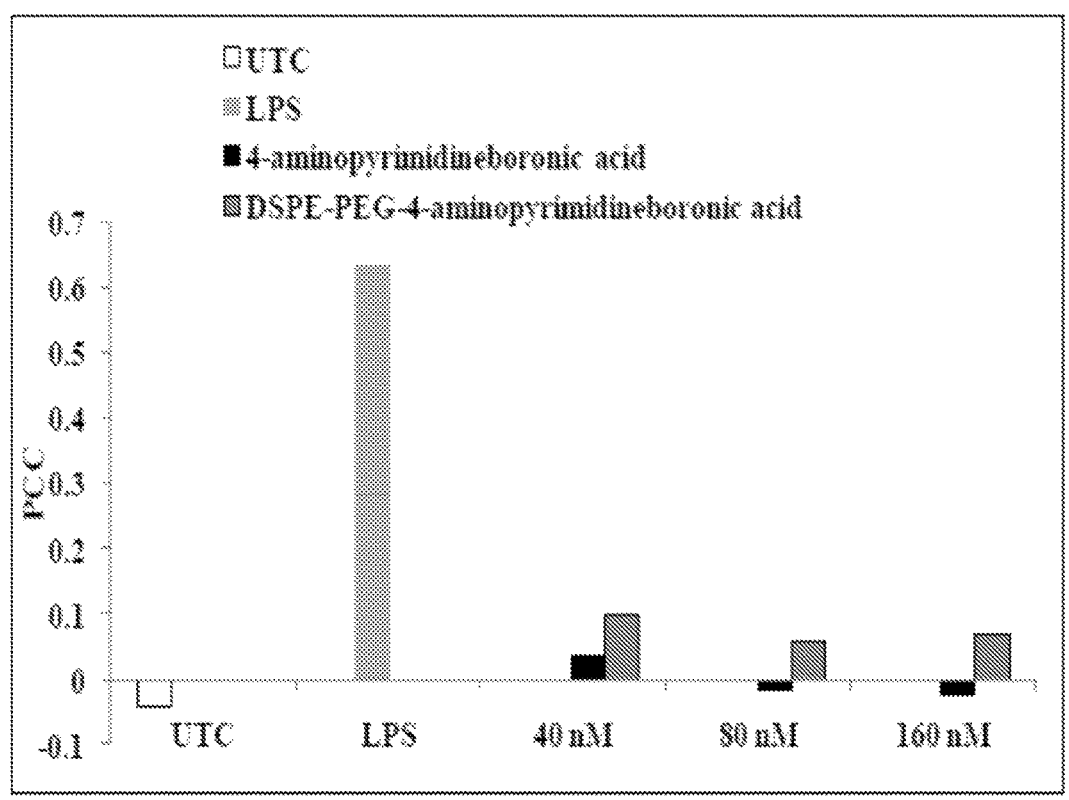
FIG. 9B illustrates a comparison of inflammatory potential between DSPE-PEG-4-aminopyrimidine boronic acid conjugate and the free ligand, 4-aminopyrimidine boronic acid.

The inflammatory potential of 4-aminopyrimidine boronic acid was compared to the conjugated ligand, namely DSPE-PEG-4-aminopyrimidine boronic acid, LSP, and an untreated control, according to the same protocols as described above in Example 6. FIG. 9B depicts the PCC between the nuclear and cytoplasmic fractions of NFκB molecule in HeLa cells. As expected, the conjugated ligand is significantly more inflammatory than the free ligand.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

What is claimed is:

1. A liposomal composition, comprising:
    a membrane, comprising:
    a first phospholipid;
    cholesterol;
    a second phospholipid, the second phospholipid being derivatized with a polymer; a third phospholipid, the third phospholipid being a phospholipid-polymer-aromatic compound conjugate,
    the phospholipid-polymer-aromatic compound conjugate being represented by:

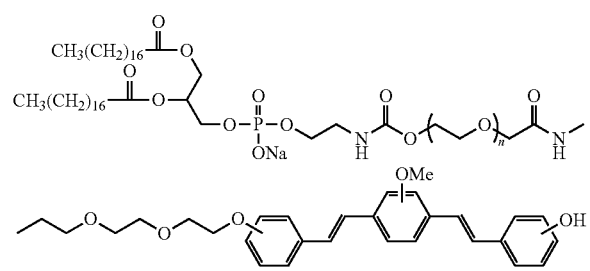

wherein n is about 10 to about 100; and
    a nonradioactive magnetic resonance imaging (MM) contrast enhancing agent at least one of encapsulated by or bound to the membrane.

2. The liposomal composition of claim 1, wherein n is about 30 to about 60.

3. The liposomal composition of claim 1, wherein:
the phospholipid-polymer-aromatic compound conjugate is represented by:

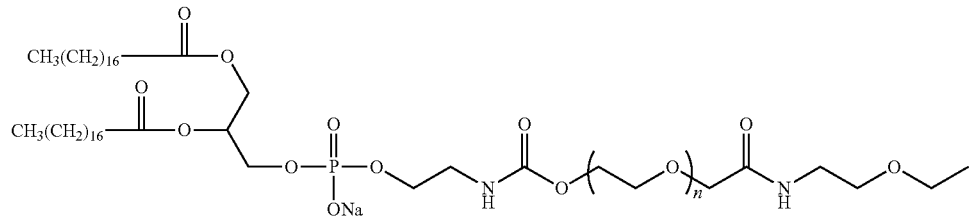

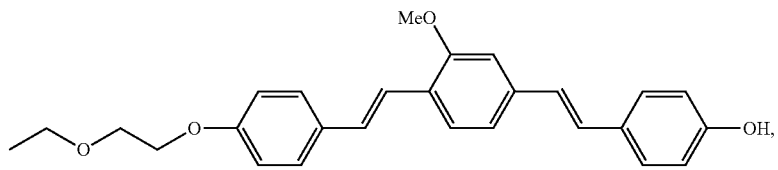

wherein n is about 10 to about 100.

4. The liposomal composition of claim 3, wherein n is about 30 to about 60.

5. The liposomal composition of claim 1, wherein the nonradioactive MRI contrast enhancing agent comprises gadolinium.

6. A method for imaging amyloid deposits in a patient, the method comprising:
introducing into the patient a detectable quantity of a liposomal composition comprising:
a membrane, comprising:
a first phospholipid;
cholesterol;
a second phospholipid, the second phospholipid derivatized with a polymer; and
a third phospholipid, the third phospholipid being a phospholipid-polymer-aromatic compound conjugate represented by:

a nonradioactive magnetic resonance imaging (MRI) contrast enhancing agent at least one of encapsulated by or bound to the membrane;

allowing sufficient time for the liposomal composition to be associated with one or more amyloid deposits; and detecting the liposomal composition associated with the one or more amyloid deposits.

7. The method of claim 6, wherein the nonradioactive MRI contrast enhancing agent comprises gadolinium.

8. The method of claim 6, wherein the detecting comprises detecting using magnetic resonance imaging.

9. The method of claim 6, wherein n is about 30 to about 60.

10. The method of claim 6, wherein the phospholipid-polymer-aromatic compound is represented by:

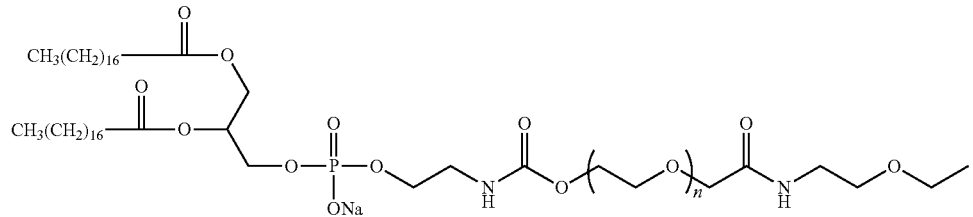

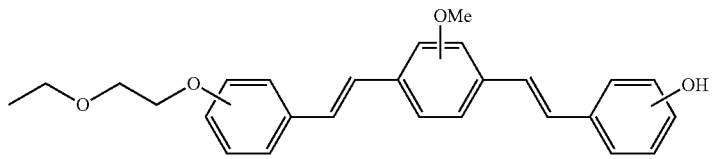

wherein n is about 10 to about 100; and

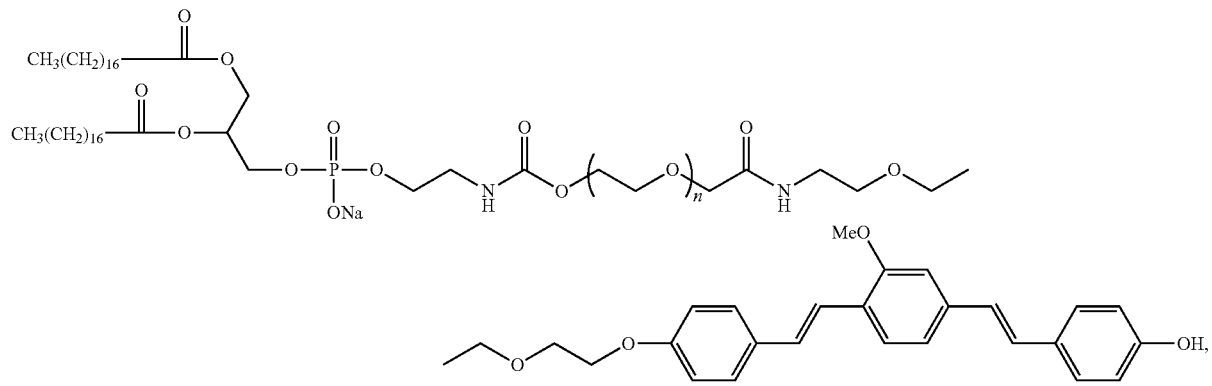
wherein n is about 10 to about 100.
11. A liposomal composition for capturing images of amyloid deposits on a patient's brain, the liposomal composition comprising:
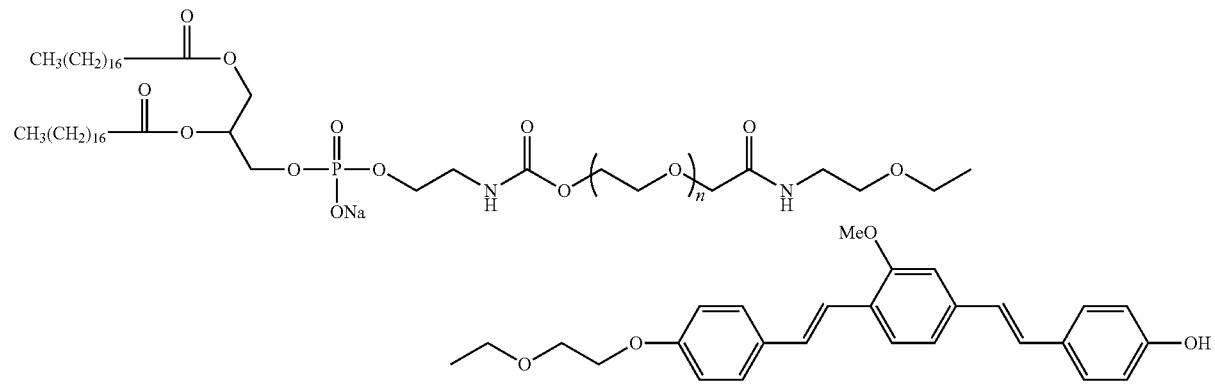
wherein: n is about 10 to about 100; and
Gd-DTPA-BSA.
12. The liposomal composition of claim 11, wherein n is about 30 to about 60.
DPPC;
cholesterol;
DSPE-mPEG-2000; and
* * * * *